United States Patent
Higuchi et al.

(10) Patent No.: US 10,451,586 B2
(45) Date of Patent: *Oct. 22, 2019

(54) GAS SENSOR SYSTEM

(71) Applicant: NGK SPARK PLUG CO., LTD., Nagoya-shi, Aichi (JP)

(72) Inventors: Yuzo Higuchi, Komaki (JP); Tomonori Uemura, Komaki (JP)

(73) Assignee: NGK SPARK PLUG CO., LTD., Aichi (JP)

( * ) Notice: Subject to any disclaimer, the term of this patent is extended or adjusted under 35 U.S.C. 154(b) by 653 days.

This patent is subject to a terminal disclaimer.

(21) Appl. No.: 14/870,398

(22) Filed: Sep. 30, 2015

(65) Prior Publication Data

US 2016/0097737 A1 Apr. 7, 2016

(30) Foreign Application Priority Data

Oct. 1, 2014 (JP) .................. 2014-203299

(51) Int. Cl.
| | |
|---|---|
| G01N 27/41 | (2006.01) |
| G01N 27/406 | (2006.01) |
| G01N 27/409 | (2006.01) |
| G01N 27/417 | (2006.01) |
| G01N 27/419 | (2006.01) |
| G01N 27/407 | (2006.01) |
| G01N 27/416 | (2006.01) |

(52) U.S. Cl.
CPC ....... *G01N 27/4175* (2013.01); *G01N 27/409* (2013.01); *G01N 27/4065* (2013.01); *G01N 27/4073* (2013.01); *G01N 27/41* (2013.01); *G01N 27/419* (2013.01); *G01N 27/4163* (2013.01)

(58) Field of Classification Search
CPC .. G01N 27/4065; G01N 27/409; G01N 27/41; G01N 27/4163; G01N 27/4073; G01N 27/4175; G01N 27/419

See application file for complete search history.

(56) References Cited

U.S. PATENT DOCUMENTS

2005/0288847 A1* 12/2005 Inoue ................. G01N 27/4175
701/114
2012/0266647 A1 10/2012 Barnikow et al.

FOREIGN PATENT DOCUMENTS

JP 2006-47278 A 2/2006

* cited by examiner

*Primary Examiner* — Mayla Gonzalez Ramos
(74) *Attorney, Agent, or Firm* — Sughrue Mion, PLLC

(57) ABSTRACT

A gas sensor system (1) including a gas sensor (2) and a sensor control section (40) including detection circuits (41), (42) and (43) for detecting the terminal potentials V1, V2, and V3 of first to third terminal T1 through T3. The sensor control section (40) includes a circuit (44) for applying an examination potential Vex to the second terminal T2, a first circuit (45) which has a predetermined resistance R1c and disconnectably connects the first terminal T1 and the second terminal T2, a second circuit (46) which has a predetermined resistance R2c and disconnectably connects the second terminal T2 and the third terminal T3, and terminal potential detection means S5 for detecting the terminal potentials V1, V2, and V3 using the detection circuits in a state in which the examination potential Vex is applied to the second terminal T2 and switches SW1 and SW2 are turned on.

15 Claims, 12 Drawing Sheets

GAS SENSOR SYSTEM

BACKGROUND OF THE INVENTION

1. Field of the Invention

The present invention relates to a gas sensor system which includes a gas sensor having an oxygen pump cell and an oxygen concentration detection cell, and a sensor control section for controlling the gas sensor.

2. Description of the Related Art

Conventionally, gas sensors such as a full-range air-fuel-ratio sensor have been known having two cells (an oxygen pump cell and an oxygen concentration detection cell) and an NOx sensor having three cells (the above-described two cells and a cell for detecting the concentration of NOx gas). Such a gas sensor constitutes a gas sensor system in cooperation with a sensor control section for controlling the gas sensor, and the gas sensor system is mounted on a vehicle or the like.

Some such gas sensors have three terminals electrically communicating with the oxygen pump cell and the oxygen concentration detection cell. Specifically, of the three terminals, first and second terminals communicate with a pair of electrodes of the oxygen pump cell. The second terminal communicates with one of a pair of electrodes of the oxygen concentration detection cell as well, and a third terminal communicates with the other electrode of the oxygen concentration detection cell. The sensor control section controls the gas sensor through these terminals.

Incidentally, in such a gas sensor system, a short anomaly may arises in which any one of the terminals of the gas sensor connected to the sensor control section may be shorted to a ground potential or a power supply potential, for example, the battery potential of a vehicle. Specifically, this may be a terminal itself or a wiring line which connects the terminal to short the cell to the ground potential or the power supply potential. Hereinafter, this state will also be expressed as "a terminal is shorted" or "short of a terminal". If electric current is supplied to the gas sensor in a state in which such a short anomaly continues, an excessively large abnormal current flows to the oxygen pump cell and/or the oxygen concentration detection cell, and the gas sensor may deteriorate or fail. Therefore, conventionally, a method of diagnosing short anomalies in a gas sensor system has been proposed.

For example, Patent Document 1 discloses an anomaly diagnosing method of supplying a current for anomaly diagnosis to each cell of a gas sensor through connection points (corresponding to the above-described terminals), and determining, based on the potential of each connection point detected when the current is supplied, a location where a short anomaly has occurred, and the source (end) of the short-circuit (short to the ground potential or short to the power supply potential).

[Patent Document 1] Japanese Patent Application Laid-Open (kokai) No. 2006-47278

Problems to be Solved by the Invention

However, in the conventional short anomaly diagnosis method described in Patent Document 1, in a state in which a gas sensor has been heated to a high temperature for activation, a current for anomaly diagnosis (anomaly diagnosing current) is supplied to each cell, and anomaly diagnosis is performed. However, in a state in which the temperature of the gas sensor is low (for example, before the gas sensor is activated), the method may fail to properly determine whether or not a short anomaly has occurred, the location where the short anomaly has occurred, and the source (end) of the short-circuit. This is because, in a state in which the temperature of the gas sensor is low; i.e., in a state in which the internal resistance of each cell is high, even when the anomaly diagnosing current is supplied to the cell, the potential of the corresponding connection point may fail to change between the case where a short to the power supply potential (battery potential) has occurred and the case where such a short has not occurred.

SUMMARY OF THE INVENTION

The present invention has been made to address the above problem, and an object thereof is to provide a gas sensor system which can determine, through diagnosis, whether or not a short anomaly of a gas sensor is present irrespective of the temperature of the gas sensor.

The above object of the invention has been achieved by providing (1) a gas sensor system comprising a gas sensor having an oxygen pump cell electrically communicating with a first terminal and a second terminal, and an oxygen concentration detection cell communicating with the second terminal and a third terminal; and a sensor control section which includes a first terminal potential detection circuit for detecting a first terminal potential of the first terminal, a second terminal potential detection circuit for detecting a second terminal potential of the second terminal, and a third terminal potential detection circuit for detecting a third terminal potential of the third terminal and which controls the gas sensor through the first terminal, the second terminal, and the third terminal. The sensor control section includes an examination potential circuit for applying to the second terminal a predetermined examination potential which is higher than a ground potential and is lower than a power supply potential of a power supply for control of the sensor control section; a first circuit for disconnectably connecting the first terminal and the second terminal, the first circuit having a resistance which is lower than an input resistance of the first terminal potential detection circuit, is lower than an internal resistance of the oxygen pump cell in a state in which the oxygen pump cell does not exhibit oxygen ion conductivity, and is higher than the internal resistance of the oxygen pump cell in a state in which the gas sensor is an activated state; a second circuit for disconnectably connecting the second terminal and the third terminal, the second circuit having a resistance which is lower than an input resistance of the third terminal potential detection circuit, is lower than an internal resistance of the oxygen concentration detection cell in a state in which the oxygen concentration detection cell does not exhibit oxygen ion conductivity, and is higher than the internal resistance of the oxygen concentration detection cell in a state in which the gas sensor is in the activated state; and terminal potential detection means for detecting the first terminal potential, the second terminal potential, and the third terminal potential using the first terminal potential detection circuit, the second terminal potential detection circuit, and the third terminal potential detection circuit in a state in which the examination potential is applied to the second terminal, and in a state in which the first circuit and the second circuit are connected.

In the gas sensor system (1), the presence/absence of short anomaly of the gas sensor can be judged irrespective of the temperature of the gas sensor. This will be described below.

In the gas sensor system (1), the first terminal and the second terminal are connected through the first circuit, and the second terminal and the third terminal are connected through the second circuit. As a result, the first circuit is connected in parallel with the oxygen pump cell, and the second circuit is connected in parallel with the oxygen concentration detection cell. In this state, the examination potential is applied to the second terminal.

Notably, the first input resistance and the second input resistance are usually 1 MΩ or higher. Meanwhile, the internal resistances of the oxygen pump cell and the oxygen concentration detection cell change greatly with their temperatures. In a state in which the oxygen pump cell and the oxygen concentration detection cell do not exhibit oxygen ion conductivity (before the temperature of the gas sensor is raised or immediately after the operation of raising the temperature has been started), the internal resistance of each cell is high (for example, 100 kΩ or higher). Meanwhile, in the activated state after the temperature of the gas sensor has been raised so as to activate the gas sensor for use, the internal resistance of each cell is about several tens of ohms through several hundreds of ohms; for example, 450 Ω or lower (in this case, the reference resistance value for determining whether or not the gas sensor has been activated is 450 Ω).

The resistance value of the first circuit (the value of the circuit resistance of the first circuit) hereinafter referred to as the "first circuit resistance" or "first circuit resistance value", is rendered lower than the first input resistance, lower than the internal resistance of the oxygen pump cell in a state in which the oxygen pump cell does not exhibit oxygen ion conductivity, and higher than the internal resistance of the oxygen pump cell in a state in which the gas sensor is in the activated state.

The resistance value of the second circuit (the value of the circuit resistance of the second circuit) hereinafter referred to as the "second circuit resistance" or "second circuit resistance value", is rendered lower than the second input resistance, lower than the internal resistance of the oxygen concentration detection cell in a state in which the oxygen concentration detection cell does not exhibit oxygen ion conductivity, and higher than the internal resistance of the oxygen concentration detection cell in a state in which the gas sensor is in the activated state.

For example, each of the first circuit resistance value and the second circuit resistance value is set to about 1 kΩ to 10 kΩ.

First the case will be considered where none of the terminals is shorted to the ground potential or the power supply potential (battery potential).

In this case, the second terminal potential detected by the second terminal potential detection circuit is equal to the examination potential applied to the second terminal.

The first terminal potential becomes equal to a potential obtained by dividing the examination potential applied to the second terminal by the combined resistance (hereinafter referred to as the "first combined resistance") of the first circuit resistance of the first circuit and the internal resistance of the oxygen pump cell connected in parallel and the input resistance of the first terminal potential detection circuit (hereinafter referred as the "first input resistance").

Similarly, the third terminal potential becomes equal to a potential obtained by dividing the examination potential applied to the second terminal by the combined resistance (hereinafter referred to as the "second combined resistance") of the second circuit resistance of the second circuit and the internal resistance of the oxygen concentration detection cell connected in parallel and the input resistance of the third terminal potential detection circuit (hereinafter referred as the "second input resistance").

The values of the first combined resistance and the second combined resistance in a state in which the oxygen pump cell and the oxygen concentration detection cell do not exhibit oxygen ion conductivity (namely, in a low-temperature state before their temperatures rise or immediately after their temperatures have started to rise) are approximately equal to the first circuit resistance value and the second circuit resistance value (1 kΩ to 10 kΩ), and the values of the first combined resistance and the second combined resistance when the gas sensor is in the activated state (namely, a high-temperature state after the sensor has been heated and activated) become lower than or approximately equal to the values of the internal resistances of the oxygen pump cell and the oxygen concentration detection cell (several tens of ohms to several hundreds of ohms). Accordingly, in either case, the first combined resistance and the second combined resistance are sufficiently lower than the first input resistance and the second input resistance (1 MΩ or higher).

Therefore, the first terminal potential produced as a result of voltage division of the examination potential by the first combined resistance and the first input resistance becomes approximately equal to the examination potential irrespective of whether the gas sensor is in the high-temperature state (state in which the internal resistance of the cell is relatively low (including the activated state)) or is in the low-temperature state (state in which the internal resistance of the cell is relatively high (including the state in which the cell does no exhibit oxygen ion conductivity)). Similarly, the third terminal potential produced as a result of voltage division of the examination potential by the second combined resistance and the second input resistance becomes approximately equal to the examination potential irrespective of whether the gas sensor is in the high-temperature state or is in the low-temperature state.

Namely, in the case where none of the terminals is shorted, all the terminal potentials of the first terminal thorough the third terminal become approximately equal to the examination potential irrespective of the temperature of the gas sensor.

Meanwhile, in the case where one of the terminals is shorted to the ground potential, at least one of the terminal potentials of the first terminal thorough the third terminal assumes a potential (≃the ground potential) lower than the examination potential.

Also, in the case where one of the terminals is shorted to the power supply potential (battery potential), at least one of the terminal potentials of the first terminal thorough the third terminal assumes a potential (≃the battery potential or the power supply potential of a power supply for control or the like) higher than the examination potential.

Therefore, irrespective of the temperature of the gas sensor, when at least one of the terminal potentials of the first terminal through the third terminal is not equal to the examination potential, a short anomaly is found to have occurred at one of the terminals.

In this manner, this gas sensor system can judge the presence/absence of short anomaly of the gas sensor irrespective of the temperature of the gas sensor.

However, there is no guarantee that the judgment as to which terminal is shorted can be made by the above-described judgment only.

This is because, in the state in which the temperature of the gas sensor is high; i.e., in the case where the internal resistance of the cell is low, in some cases, the terminals which are not shorted have potentials close to the potential (the ground potential or the power supply potential) of the terminal which is shorted. Since the internal resistance of the cell located between the location where the short has occurred and the location where no short has occurred is low, a large (discharge or sink) current is output from the examination potential circuit, and the examination potential circuit fails to maintain the predetermined examination potential (for example, +2.5 V), whereby the potential difference produced between the terminals may become small.

For example, in the case where the internal resistance of the oxygen pump cell of the gas sensor operating in the activated state is about 80Ω, if the first circuit resistance value of the first circuit is assumed to be 1 kΩ, the value of the combined resistance (the first combined resistance) of the first circuit resistance of the first circuit and the internal resistance of the oxygen pump cell present between the first terminal and the second terminal becomes about 74Ω. In an assumed case where the examination potential applied to the second terminal is set to, for example, +2.5 V and the first terminal is shorted to a battery potential of +12 V, in order to maintain the second terminal potential at the examination potential, the examination potential circuit must have an output performance which allows the circuit to sink a current of about 128 mA.

In contrast, in the case where the output performance of the examination potential circuit is not sufficient, the sinkable current is limited, and the output voltage increases. Namely, not only the first terminal potential of the shorted first terminal, but also the second terminal potential of the second terminal not shorted assumes a potential closer to the battery potential than the predetermined examination potential (+2.5 V in the above-described example).

As described above, when the gas sensor is in the high-temperature state (e.g., the activated state), the gas sensor system may fail to properly judge the location where the short anomaly of the gas sensor has occurred (which terminal is shorted) and the source (end) of the short-circuit (short to the ground potential or short to the power supply potential).

Meanwhile, in a state in which the temperature of the gas sensor is low, such as a state before the temperature of the gas sensor is raised and a state immediately after the operation of raising the temperature has been started); i.e., in the state in which the internal resistances of the cells are high (including the state in which the cells do not exhibit oxygen ion conductivity), even when one of the terminals is shorted to the ground potential or the power supply potential, the current output performance of the examination potential circuit imposes no restriction. Since the combination of the potentials of the terminals is a peculiar combination corresponding to the state of occurrence of the short anomaly, the location where the short anomaly has occurred and the source (end) of the short-circuit can be judged.

Accordingly, in this gas sensor system, in the case where the temperature of the gas sensor is lower than that in the activated state (specifically, the gas sensor is in a state in which its temperature is lower than a judgment temperature for judging whether or not the gas sensor has been activated (i.e., a low-temperature state described below)), not only the presence/absence of short anomaly of the gas sensor, but also the location where the short anomaly has occurred and the source (end) of the short-circuit can be determined, through diagnosis, based on the detected first terminal potential, the detected second terminal potential, and the detected third terminal potential.

Notably, the first circuit resistance value and the second circuit resistance value are preferably set to respective values sufficiently lower than (lower than one-hundredth of) the first input resistance of the first terminal potential detection circuit and the second input resistance of the second terminal potential detection circuit (1 MΩ or higher). In addition, the first circuit resistance value and the second circuit resistance value are preferably set to respective values at least ten times the internal resistances of the oxygen pump cell and the oxygen concentration detection cell at the time when the gas sensor is in the activated state. For example, in the case where the internal resistances of the oxygen pump cell and the oxygen concentration detection cell at the time when the gas sensor is in the activated state are several tens of ohms through several hundreds of ohms, the first circuit resistance value and the second circuit resistance value are preferably set to several hundreds of ohms through several thousands of ohms, which are about ten times the internal resistances.

Even in the case where a short anomaly occurs and a current flows out from or flows into the examination potential circuit, within a range within which the predetermined examination potential can be maintained stably, the location where the short anomaly of the gas sensor has occurred and the source (end) of the short-circuit can be determined through diagnosis. Therefore, the judgment as to whether or not the gas sensor is in the low-temperature state is preferably made by judging whether or not the temperature of the gas sensor falls within a portion of a temperature range lower than that in the activated state, in which portion the examination potential circuit can maintain the examination potential in a state in which a short anomaly has occurred. Specifically, the judgment is preferably made by using a threshold temperature determined as follows. Within a temperature range lower than that in the activated state (for example, a temperature range within which the internal resistances of the cells become higher than 450 Ω when a reference resistance value for the internal resistances of the cells used for judging whether or not the gas sensor has been activated is 450 Ω), the highest temperature at which the examination potential circuit can maintain the examination potential in a state in which a short anomaly has occurred is determined (a temperature which falls within a temperature range within which the internal resistances of the cells are higher than 450 Ω and at which the internal resistances of the cells become the minimum resistances at which the examination potential can be maintained), and a temperature equal to or lower than the highest temperature is used as the threshold temperature. In the state in which the temperature of the gas sensor (the oxygen pump cell and the oxygen concentration detection cell) falls within the temperature range lower than the threshold temperature (the low-temperature state), in addition to the presence/absence of short anomaly, the location of occurrence of short anomaly and the source (end) of the short-circuit can be determined through diagnosis.

In a preferred embodiment (2) of the above-described gas sensor system (1), the sensor control section includes short presence/absence judgment means for judging whether or not a short anomaly of the gas sensor is present based on the first terminal potential, the second terminal potential, and the third terminal potential detected by the terminal potential detection means.

This gas sensor system includes the short presence/absence judgment means, and the presence/absence of short anomaly of the gas sensor is judged by this short presence/absence judgment means.

As described above, in this system, as a result of connection of the first circuit and the second circuit, the first circuit is connected in parallel with the oxygen pump cell, and the second circuit is connected in parallel with the oxygen concentration detection cell. Therefore, the presence/absence of short anomaly of the gas sensor can be judged not only in the state in which the internal resistances of the cells are low (the temperature of the gas sensor is high), but also in the state in which the internal resistances of the cells are high (the temperature of the gas sensor is low).

Accordingly, this system can judge the presence/absence of short anomaly of the gas sensor by the system itself irrespective of the temperature of the gas sensor.

In another preferred embodiment (3) of the above-described gas sensor system (2), preferably, the short presence/absence judgment means judges whether or not all of the detected first terminal potential, the detected second terminal potential, and the detected third terminal potential are equal to the examination potential.

As described above, in the case where none of the terminals is shorted, when the examination potential is applied to the second terminal, all of the first terminal potential, the second terminal potential, and the third terminal potential become equal to the examination potential.

Accordingly, in this gas sensor system, the presence/absence of short anomaly of the gas sensor can be judged properly by the above-mentioned short presence/absence judgment means based on the detected first terminal potential, the detected second terminal potential, and the detected third terminal potential.

In yet another preferred embodiment (4) of the gas sensor systems (2) or (3) above, the sensor control section includes short state judgment means, operable when the short presence/absence judgment means judges that a short anomaly is present, for judging a short state, including a location where the short anomaly of the gas sensor has occurred and a source of the short-circuit, based on the first terminal potential, the second terminal potential, and the third terminal potential detected by the terminal potential detection means, when the gas sensor is in a low-temperature state in which its temperature is lower than in the activated state.

As described above, in the state in which the temperature of the gas sensor is high (including the activated state), the location where a short anomaly of the gas sensor has occurred and the source (end) of the short-circuit cannot be determined properly in some cases. However, when the gas sensor is in the low-temperature state in which the temperature of the gas sensor is lower than in the activated state (in a state in which the temperature is lower than the temperature for determining whether or not the gas sensor has been activated), the system can properly judge, through diagnosis, the location where the short anomaly has occurred (which terminal is shorted) and the source or end of the short-circuit (short to the ground potential or short to the power supply potential) based on the first terminal potential through the third terminal potential.

This system includes short state judgment means for judging a short state, including the location where the short anomaly has occurred and the source (end) of the short-circuit, when the temperature of the gas sensor is low. Therefore, it is possible to determine not only the presence/absence of a short anomaly but also the short state, and to report this information to an external device such as an ECU and/or to take appropriate measures.

Examples of the method of judging whether or not the gas sensor is in the low-temperature state include a method of detecting the internal resistance of each cell of the gas sensor and judging whether or not the detected internal resistance is higher than a predetermined threshold resistance, and a method of detecting the temperature of the gas sensor (cells) using a temperature sensor and judging whether or not the detected temperature is lower than a predetermined threshold temperature.

In another method, the judgment as to whether or not the gas sensor is in the low-temperature state is made based on the history of use of the system (for example, the time between stopping and restarting the engine). In the case where the gas sensor is a heater-incorporated sensor, the judgment as to whether or not the gas sensor is in the low-temperature state can be made based on the heater resistance or the cumulative energization time of the heater.

In yet another preferred embodiment (5) of the above-described gas sensor system (4), the short state judgment means judges, based on the detected first terminal potential, the detected second terminal potential, and the detected third terminal potential, six types of short states, the six types of short states including a first short-to-GND state in which a first wiring line for connecting the oxygen pump cell to the first terminal is shorted to the ground potential, a second short-to-GND state in which a second wiring line for connecting the oxygen pump cell and the oxygen concentration detection cell to the second terminal is shorted to the ground potential, a third short-to-GND state in which a third wiring line for connecting the oxygen concentration detection cell to the third terminal is shorted to the ground potential, a first short-to-power state in which the first wiring line is shorted to a power supply potential, a second short-to-power state in which the second wiring line is shorted to the power supply potential, and a third short-to-power state in which the third wiring line is shorted to the power supply potential.

In this gas sensor system, the short state judgment means judges six type of short states in total (three types of short-to-GND states and three types of short-to-power states) based on the first terminal potential, the second terminal potential, and the third terminal potential. Therefore, when a short anomaly occurs, its short state can be judged properly.

In yet another preferred embodiment (6) of the above-described gas sensor system (5), the short state judgment means judges, based on the detected first terminal potential, the detected second terminal potential, and the detected third terminal potential, that the gas sensor is in the first short-to-GND state when the second terminal potential and the third terminal potential are equal to the examination potential and the first terminal potential is lower than the examination potential, that the gas sensor is in the second short-to-GND state when all of the first terminal potential, the second terminal potential, and the third terminal potential are lower than the examination potential, that the gas sensor is in the third short-to-GND state when the first terminal potential and the second terminal potential are equal to the examination potential and the third terminal potential is lower than the examination potential, that the gas sensor is in the first short-to-power state when the second terminal potential and the third terminal potential are equal to the examination potential and the first terminal potential is higher than the examination potential, that the gas sensor is in the second short-to-power state when all of the first terminal potential, the second terminal potential, and the third terminal potential are higher than the examination potential, and that the gas sensor is in the third short-to-power state when the first terminal potential and the second terminal potential are equal to the examination potential and the third terminal potential is higher than the examination potential.

In this gas sensor system, the short state judgment means distinguishes six types of states from one another based on the potentials of the terminals. Therefore, the six types of short states can be judged properly.

As described above, in the state in which none of the first wiring line communicating with the first terminal, the second wiring line communicating with the second terminal, and the third wiring line communicating with the third terminal is shorted, all the first terminal potential, the second terminal potential, and the third terminal potential become equal to the examination potential.

In contrast, when a short anomaly occurs, the terminal potentials change as follow.

First, in the case where the first wiring line is shorted to the ground potential in a state in which none of the second wiring line and the third wiring line is shorted (first short-to-GND state), the second terminal potential and the third terminal potential become equal to the examination potential and the first terminal potential becomes a potential (≅the ground potential) lower than the examination potential. Therefore, the first wiring line is found to be shorted to the ground potential.

In the case where the first wiring line is shorted to the power supply potential (battery potential) in a state in which none of the second wiring line and the third wiring line is shorted (first short-to-power state), the second terminal potential and the third terminal potential become equal to the examination potential, and the first terminal potential assumes a potential (≅the battery potential or the power supply potential of a power supply for control or the like in the case where a voltage limiter circuit for protection is provided for the first terminal and other terminals) higher than the examination potential. Therefore, the first wiring line is found to be shorted to the power supply potential (the battery potential).

In the case where the third wiring line is shorted to the ground potential in a state in which none of the first wiring line and the second wiring line is shorted (third short-to-GND state), the first terminal potential and the second terminal potential become equal to the examination potential and the third terminal potential assumes a potential lower than the examination potential. Therefore, the third wiring line is found to be shorted to the ground potential.

In the case where the third wiring line is shorted to the power supply potential in a state in which none of the first wiring line and the second wiring line is shorted (third short-to-power state), the first terminal potential and the second terminal potential become equal to the examination potential and the third terminal potential assumes a potential higher than the examination potential. Therefore, the third wiring line is found to be shorted to the power supply potential.

In the case where the second wiring line is shorted to the ground potential in a state in which none of the first wiring line and the third wiring line is shorted (second short-to-GND state), all of the first terminal potential, the second terminal potential, and the third terminal potential assumes a potential lower than the examination potential. Therefore, the second wiring line is found to be shorted to the ground potential.

In the case where the second wiring line is shorted to the power supply potential in a state in which none of the first wiring line and the third wiring line is shorted (second short-to-power state), all of the first terminal potential, the second terminal potential, and the third terminal potential assumes a potential higher than the examination potential. Therefore, the second wiring line is found to be shorted to the power supply potential.

In this manner, this system can properly judge the six types of states of short anomaly in accordance with the potentials of the terminals.

In yet another preferred embodiment (7) of the above-described gas sensor system (4), the sensor control section includes hot restart judgment means for judging immediately after startup of the system whether or not the startup of the system is a hot restart; and first waiting means for waiting until the gas sensor has assumed the low-temperature state, prior to judgment by the short state judgment means, when the hot restart judgment means judges that the startup is the hot restart and the short presence/absence judgment means judges that a short anomaly is present.

In this gas sensor system, in the case where the system judges that the startup is a hot restart and a short anomaly is present, the system waits until the gas sensor has assumed the low-temperature state prior to the performance of judgment by the short state judgment means.

As described above, in the case where the temperature of the gas sensor is high, the internal resistances of the oxygen pump cell and the oxygen concentration detection cell are low as compared with those in the case where the temperature of the gas sensor is low. Therefore, when one of the first through third terminals is shorted, the terminals not shorted may assume potentials close to the potential of the shorted terminal, which makes it impossible to judge which one of the terminals is shorted. Meanwhile, as described above, the judgment of presence/absence of a short anomaly can be performed even when the gas sensor is in the high-temperature state such as an activated state.

In view of the above, in this system, in the case where the startup is a hot restart, the judgment of the presence/absence of a short anomaly is performed when the gas sensor is in the high-temperature state, and the judgment of the short state is performed after waiting until the gas sensor has assumed a low-temperature state. As a result, when no short anomaly is present, the system can proceed to the next step in the state in which the temperature of the gas sensor is still high. In addition, in the case of a hot restart as well, the steps up to the judgment of the short state can be performed properly.

Notably, the hot restart refers to a case where the system is started in a state in which the temperature of the gas sensor is high; namely, the temperature of the gas sensor is high immediately after system startup. An example of the method of judging whether or not the startup is a hot restart is a method of judging whether or not the startup is a hot restart based on the history of use of the system, for example, by judging whether or not the time between stopping and restarting the engine is shorter than a predetermined time (for example, 30 sec or shorter).

An example of the method of waiting until the gas sensor has assumed a low-temperature state is a method of waiting for elapse of a predetermined time without operating a heater for heating the gas sensor.

In yet another preferred embodiment (8) of the above-described gas sensor system (4), the sensor control section includes second waiting means for waiting until the gas sensor has assumed the low-temperature state, prior to judgment by the short state judgment means, when the short presence/absence judgment means judges that a short anomaly is present while the gas sensor is operating in the activated state.

In this gas sensor system, in the case where the system judges that a short anomaly is present while the gas sensor is operating in the activated state, the system determines the short state after waiting until the gas sensor has assumed the low-temperature state.

As a result, this system can properly determine the short state not only after the startup of the system, but also in a period during which the gas sensor is operating.

Notably, examples of the method of judging the presence/absence of short anomaly while the gas sensor is operating include a method of generating a timer interruption, while the gas sensor is operating so as to periodically judge the presence/absence of a short anomaly, and a method of obtaining information of the operating state of the vehicle from the ECU and judging the presence/absence of a short anomaly when the vehicle assumes a predetermined operating state.

Also, in the case where the gas sensor is a heater-incorporated sensor, an example of the method of waiting until the state of the gas sensor changes from the activated state to the low-temperature state is a method of stopping the supply of electric current to the heater and waiting for elapse of a predetermined time.

In yet another preferred embodiment (9) the above-described gas sensor system (4), the sensor control section includes a first potential switch for applying the examination potential of the examination potential circuit to the second terminal; and first cutoff means for turning off the first potential switch when the short presence/absence judgment means judges that a short anomaly is present.

In this gas sensor system, in the case where the system judges that a short anomaly is present, application of the examination potential is cut-off. As a result, in the case where a short anomaly is present, application of the examination potential to the second terminal is not continued.

In yet another preferred embodiment (10) of the above-described gas sensor system (9), the first cutoff means turns off the first potential switch, and disconnects the first circuit and the second circuit.

In this gas sensor system, in the case where the system judges that a short anomaly is present, the first potential switch is turned off and the first and second circuits are disconnected. As a result, in the case where the gas sensor has a short anomaly, the connections between the terminals of the gas sensor established by the first circuit and the second circuit are broken, whereby the states of the terminals can be returned to the initial states before diagnosis of a short anomaly.

In yet another preferred embodiment (11) of the above-described gas sensor system (4), the gas sensor internally has a measurement chamber into which a gas under measurement is introduced and a reference oxygen chamber in which a reference oxygen atmosphere is generated; the oxygen concentration detection cell has a first detection electrode which faces the reference oxygen chamber and electrically communicates with the third terminal and a second detection electrode exposed to the measurement chamber and electrically communicates with the second terminal; and the sensor control section includes a detection cell current output circuit for supplying a detection cell current to the oxygen concentration detection cell through the third terminal, a first current switch for turning on and turning off the supply of the detection cell current from the detection cell current output circuit to the oxygen concentration detection cell through the third terminal, second cutoff means for turning off the first current switch in a period during which the short presence/absence judgment means judges whether or not a short anomaly is present, and first cutoff maintaining means for maintaining the first current switch in an off state when the short presence/absence judgment means judges that a short anomaly is present.

In this gas sensor system, in the case where the gas sensor is judged to have a short anomaly, the state is maintained in which a detection cell current (for example, a fixed minute current for pumping oxygen into the reference oxygen chamber and a current for detecting the internal resistance) supplied to the oxygen concentration detection cell is cut-off. Therefore, it is possible to prevent blackening of the oxygen concentration detection cell, which blackening would otherwise occur when the detection cell current is supplied in the state in which a short anomaly continues.

In yet another preferred embodiment (12) the above-described gas sensor system (4), the gas sensor internally has a measurement chamber into which a gas under measurement is introduced; the oxygen pump cell has a first pump electrode disposed outside the measurement chamber which electrically communicates with the first terminal and a second pump electrode exposed to the measurement chamber and which electrically communicates with the second terminal; and the sensor control section includes a pump current output circuit for supplying a pump current to the oxygen pump cell through the first terminal, a second current switch for turning on and turning off supply of the pump current from the pump current output circuit to the oxygen pump cell through the first terminal, third cutoff means for turning off the second current switch in a period during which the short presence/absence judgment means judges whether or not a short anomaly is present, and second cutoff maintaining means for maintaining the second current switch in the off state when the short presence/absence judgment means judges that a short anomaly is present.

In this gas sensor system, in the case where the gas sensor is judged to have a short anomaly, the pump current is maintained in a cut-off state. Therefore, it is possible to prevent blackening the oxygen pump cell, which blackening would otherwise occur when the pump current is supplied in the state in which a short anomaly continues.

In yet another preferred embodiment (13) of the above-described gas sensor system (4), the examination potential circuit also functions as a reference potential circuit which applies a reference potential to the second terminal after the gas sensor is activated.

In this gas sensor system, the examination potential circuit also serves as a reference potential circuit for applying the reference potential after the gas sensor is activated. Therefore, it is unnecessary to provide a dedicated examination potential circuit for diagnosis of a short anomaly.

In yet another preferred embodiment (14) of the above-described gas sensor system (13), the sensor control section includes a second potential switch for turning on and turning off the application of the examination potential and the reference potential from the reference potential circuit to the second terminal, and fourth cutoff means for turning off the second potential switch when the short presence/absence judgment means judges that a short anomaly is present.

In this gas sensor system, in the case where the gas sensor is judged to have a short anomaly, application of the examination potential and the reference potential is turned off. Therefore, it is possible to prevent blackening of the oxygen pump cell and the oxygen concentration detection cell, which blackening would otherwise occur when the examination potential or the reference potential is applied in a state in which a short anomaly continues.

DESCRIPTION OF SYMBOLS

Figure 1:
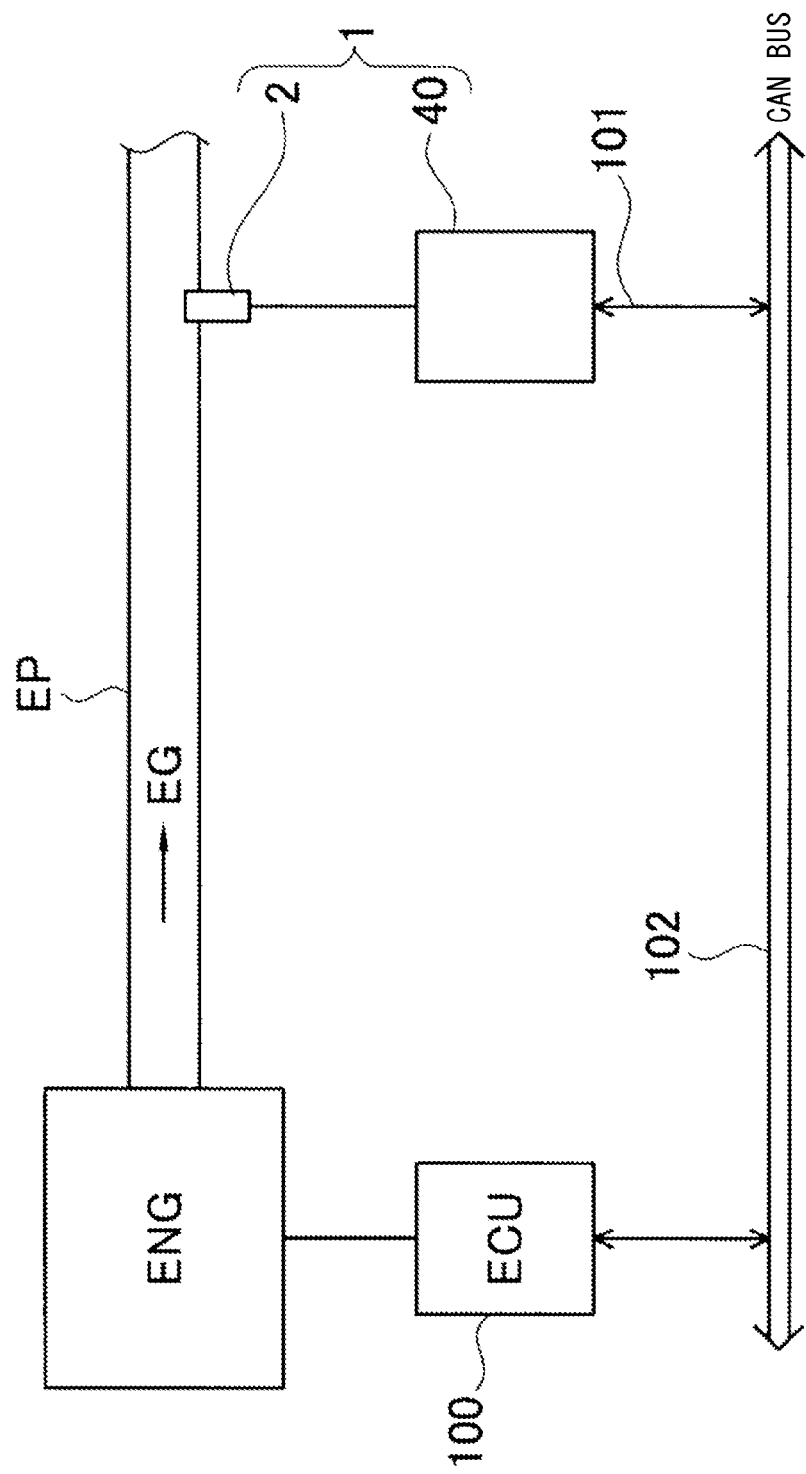
FIG. 1 is an explanatory diagram showing the overall configuration of an engine system in which a gas sensor system according to an embodiment is used for control of an internal combustion engine of a vehicle.

Reference symbols used to identify various features in the drawings include the following.
ENG: internal combustion engine (engine)
EP: exhaust pipe
EG: exhaust gas (gas under measurement)
100: ECU
1: gas sensor system
2: gas sensor
3: sensor element section
14: oxygen pump cell
12: first pump electrode
16: second pump electrode
24: oxygen concentration detection cell
28: first detection electrode
22: second detection electrode
20: measurement chamber
26: reference oxygen chamber
80: heater section
Ip: pump current
Icp: minute current (detection cell current)
T1: first terminal
T2: second terminal
T3: third terminal
L1: first wiring line
L2: second wiring line
L3: third wiring line
V1: first terminal potential
V2: second terminal potential
V3: third terminal potential
Vref: reference potential
Vex: examination potential
30: digital signal processor
40: sensor control section
41: A/D converter (first terminal potential detection circuit)
42: A/D converter (second terminal potential detection circuit)
43: A/D converter (third terminal potential detection circuit)
44: operational amplifier (examination potential circuit, reference potential circuit)
45: first circuit
R1: first resistor
R1r: first resistance
R1c: resistance of the first circuit
SW1: first switch
46: second circuit
R2: second resistor
R2r: second resistance
R2c: resistance of the second circuit
SW2: second switch
47: D/A converter (pump current output circuit)
48: D/A converter (detection cell current output circuit)
SW3: third switch (second current switch)
SW4: fourth switch (first potential switch, second potential switch)
SW5: fifth switch (first current switch)
S1: hot restart judgment means
S5, S15, S22: terminal potential detection means
S6, S16: short presence/absence judgment means
S8 (S801-S818), S23 (S2301-S2320): short state judgment means
S18-S19: first waiting means, second waiting means
S7, S17, S24: first cutoff means, first cutoff maintaining means, second cutoff maintaining means, fourth cutoff means S2, S12: second cutoff means, third cutoff means

DETAILED DESCRIPTION OF THE PREFERRED EMBODIMENTS

The present invention will next be described in detail with reference to the drawings. However, the present invention should not be construed as being limited thereto.

Figure 2:
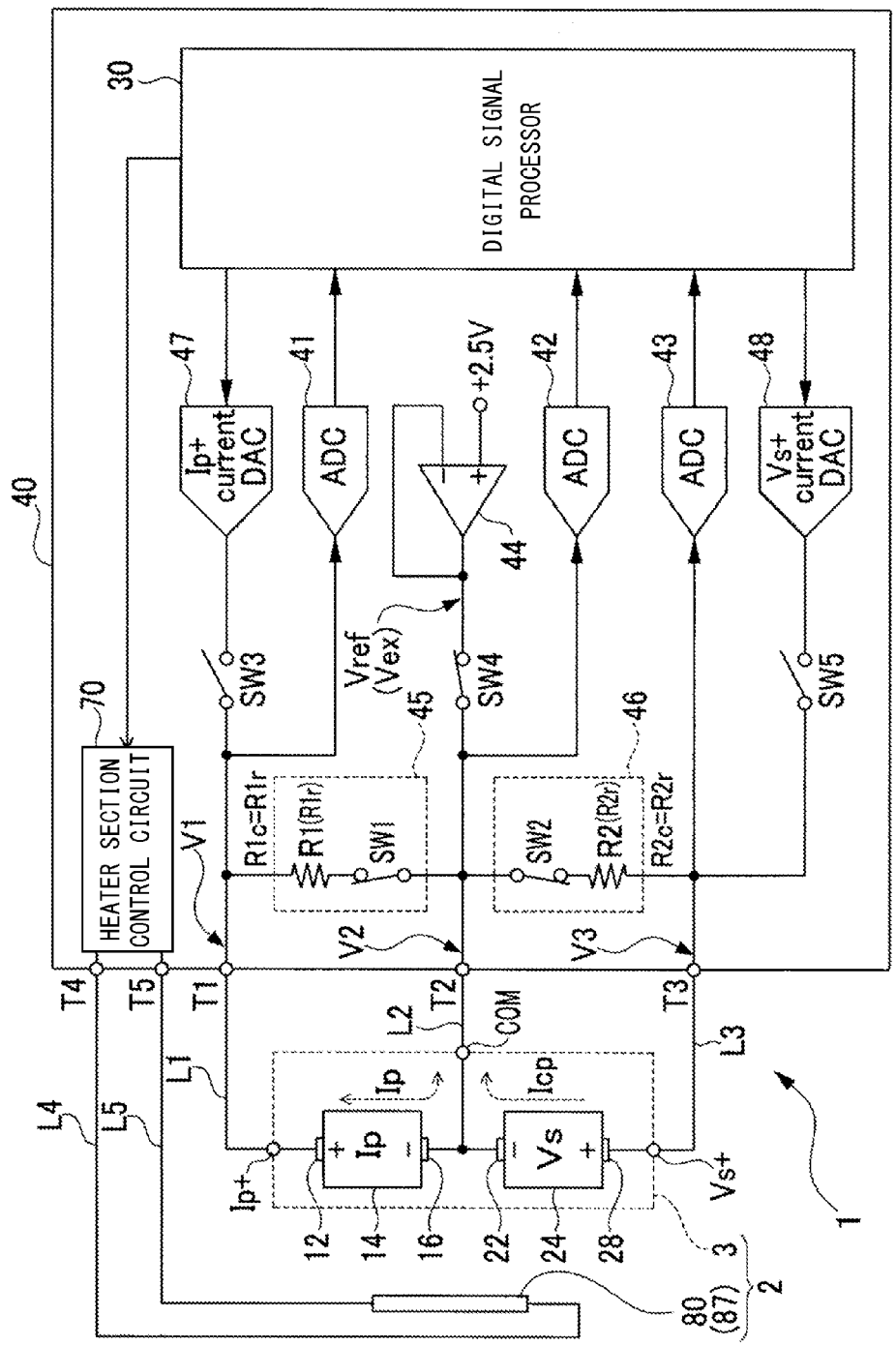
FIG. 2 is an explanatory diagram showing the overall configuration of the gas sensor system according to the embodiment.

FIG. 1 is a diagram showing the overall configuration of an engine system in which a gas sensor system 1 according to the present embodiment is used for control of an internal combustion engine of a vehicle. FIG. 2 is a diagram showing the overall configuration of the gas sensor system 1.

This gas sensor system 1 includes a gas sensor 2 attached to an exhaust pipe EP of an internal combustion engine ENG (engine) of a vehicle (not shown), and a sensor control section 40 for controlling the gas sensor 2.

Notably, the gas sensor 2 is an air-fuel-ratio sensor (full-range air-fuel-ratio sensor) which linearly detects the concentration of oxygen (air-fuel ratio) within exhaust gas EG (gas under measurement). The detected oxygen concentration (air-fuel ratio) is used for air-fuel-ratio feedback control of the internal combustion engine. As shown in FIG. 2, this gas sensor 2 has a sensor element section 3 for detecting the oxygen concentration and a heater section 80 for heating the sensor element section 3.

The sensor control section 40 is connected to the gas sensor 2 and controls the same. The gas sensor system 1 is connected to a CAN bus 102 of the vehicle through a connection bus 101, and can exchange data with an ECU 100 through transmission and reception of data. The sensor control section 40 is composed of an ASIC (Application Specific IC), and includes a digital signal processor 30, a heater section control circuit 70 for controlling the heater section 80 as well as a circuit for controlling the sensor element section 3 of the gas sensor 2.

Figure 3:
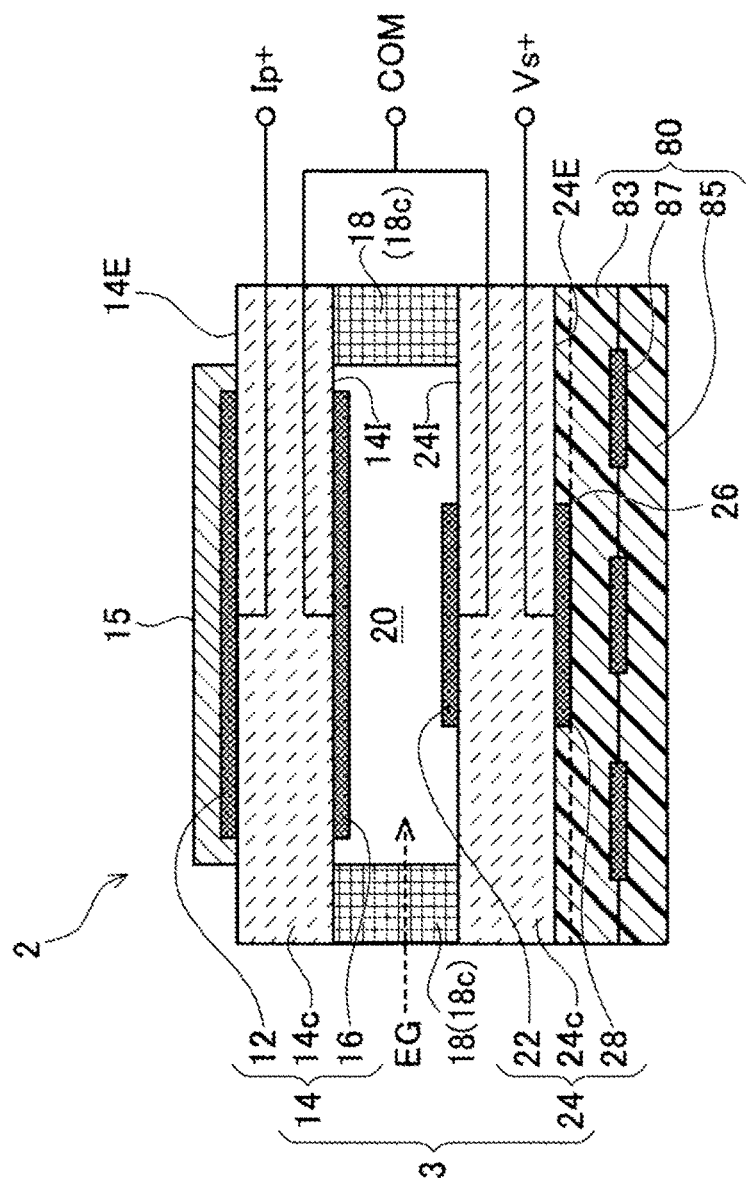
FIG. 3 is a schematic cross-sectional view of a gas sensor of the gas sensor system according to the embodiment.

First, the gas sensor 2 will be described. FIG. 3 is a schematic view showing the structure of the gas sensor 2. The sensor element section 3 of the gas sensor 2 is a laminate obtained by stacking an oxygen pump cell 14, a porous layer 18, and an oxygen concentration detection cell 24 in this order. The heater section 80 is stacked on the sensor element section 3.

The oxygen pump cell 14 has, as a substrate, an electrolyte layer 14c (a plate-shaped solid electrolyte member mainly made of zirconia and having oxygen ion conductivity), and a pair of electrodes 12 and 16 (porous electrodes) mainly made of porous platinum are formed on opposing surfaces of the electrolyte layer 14c. Specifically, the first pump electrode 12 is formed on an outer surface 14E which is one surface (located on the upper side in FIG. 3) of the electrolyte layer 14c, and the second pump electrode 16 is formed on an inner surface 14I which is the other (opposing) surface (located on the lower side in FIG. 3) of the electrolyte layer 14c.

Similarly, the oxygen concentration detection cell 24 has, as a substrate, an electrolyte layer 24c (a plate-shaped solid electrolyte member mainly made of zirconia and having oxygen ion conductivity), and a pair of electrodes 22 and 28 (porous electrodes) mainly made of porous platinum are formed on opposing surfaces of the electrolyte layer 24c. Specifically, the first detection electrode 28 is formed on an outer surface 24E which is one surface (located on the lower side in FIG. 3) of the electrolyte layer 24c, and the second detection electrode 22 is formed on an inner surface 24I which is the other (opposing) surface (located on the upper side in FIG. 3) of the electrolyte layer 24c.

The inner surface 14I of the electrolyte layer 14c of the oxygen pump cell 14 faces the inner surface 24I of the electrolyte layer 24c of the oxygen concentration detection cell 24, and the porous layer 18 is sandwiched between the electrolyte layer 14c and the electrolyte layer 24c. The porous layer 18 has porous wall portions 18c extending along the edges of the inner surface 14I of the electrolyte layer 14c and the inner surface 24I of the electrolyte layer 24c. The internal space of the porous layer 18 surrounded by the porous wall portions 18c, the electrolyte layer 14c, and the electrolyte layer 24c serves as a hollow measurement chamber 20 into which the exhaust gas EG can be introduced. Notably, the porous layer 18 allows the exhaust gas EG to flow into the measurement chamber 20, and restricts the inflow speed of the exhaust gas EG.

The second pump electrode 16 of the oxygen pump cell 14 and the second detection electrode 22 of the oxygen concentration detection cell 24 are exposed to the atmosphere within the measurement chamber 20. These electrodes 16 and 22 are electrically connected with each other and are connected to a COM terminal of the sensor element section 3. The first pump electrode 12 of the oxygen pump cell 14 is connected to an Ip+ terminal of the sensor element section 3, and the first detection electrode 28 of the oxygen concentration detection cell 24 is connected to a Vs+ terminal of the sensor element section 3.

The entirety of the first pump electrode 12 of the oxygen pump cell 14 is covered with a protection layer 15 for suppressing poisoning of the first pump electrode 12. The protection layer 15 is formed of porous ceramic or the like and is disposed in a flow path through which the exhaust gas EG flows. The exhaust gas EG can reach the first pump electrode 12 through the protection layer 15.

The heater section 80 is stacked on the outer surface 24E of the electrolyte layer 24c of the oxygen concentration detection cell 24, and has a structure in which a heater resistor formed of a conductor 87 is sandwiched between a pair of alumina sheets 83 and 85. Upon raising the temperature of the sensor element section 3 by energizing the heater section 80, the electrolyte layers 14c and 24c of the sensor element section 3 are activated. As a result, oxygen ions become capable of moving within the electrolyte layers 14c and 24c.

Also, the alumina sheet 83 of the heater section 80 covers the entirety of the first detection electrode 28 of the oxygen concentration detection cell 24 to thereby seal the first detection electrode 28. Notably, a space (hole) inside the first detection electrode 28 (porous electrode) constitutes a reference oxygen chamber 26, and functions as an internal oxygen reference source as described below.

Next, the gas sensor system 1 will be described with reference to FIG. 2. As described above, the sensor control section 40 is constituted by an ASIC including the digital signal processor 30 (hereinafter also referred to as the "processor 30" for simplicity). This sensor control section 40 has a first terminal T1, a second terminal T2, and a third terminal T3, and controls the sensor element section 3 of the gas sensor 2 through these terminals. Notably, the first terminal T1 is connected to the Ip+ terminal of the sensor element section 3 through a first wiring line L1. The second terminal T2 is connected to the COM terminal of the sensor element section 3 through a second wiring line L2. The third terminal T3 is connected to the Vs+ terminal of the sensor element section 3 through a third wiring line L3.

The sensor control section 40 has A/D converters 41, 42, and 43 connected to the first terminal T1, the second terminal T2, and the third terminal T3, respectively.

The A/D converter 41 detects a first terminal potential V1 of the first terminal T1, converts it to a digital signal, and inputs the digital signal to the processor 30. Similarly, the A/D converter 42 detects a second terminal potential V2 of the second terminal T2, converts it to a digital signal, and inputs the digital signal to the processor 30. Similarly, the A/D converter 43 detects a third terminal potential V3 of the third terminal T3, converts it to a digital signal, and inputs the digital signal to the processor 30.

Notably, the A/D converters 41, 42, and 43 are used for PID (proportional-integral-derivative) control of pump current Ip, and are also used when a short anomaly of the gas sensor 2 is diagnosed as described below.

A first circuit 45 including a first resistor R1 and a first switch SW1 is connected between the first terminal T1 and the second terminal T2. The first resistance value R1$r$ of the first resistor R1 is 1 k$\Omega$. The first switch SW1 either connects the first terminal T1 and the second terminal T2 via the first resistor R1, or breaks the connection. Notably, the resistance value (on resistance) of the first switch SW1 is negligibly low as compared with the first resistance value R1$r$. Also, in the present embodiment, the resistance value R1$c$ of the first circuit 45 (the value of the circuit resistance of the first circuit 45)=the first resistance value R1$r$=1 k$\Omega$.

The first circuit 45 having this resistance value R1c (=the first resistance value R1r) disconnectably connects the first terminal T1 and the second terminal T2. Notably, the resistance value R1c (=the first resistance value R1r) of the first circuit 45 is rendered lower than a value (1 MΩ or higher) of the input resistance of the A/D converter 41 for detecting the first terminal potential V1 and lower than a value (100 kΩ or higher) of the internal resistance of the oxygen pump cell 14 in a state in which the oxygen pump cell 14 does not exhibit oxygen ion conductivity. Meanwhile, the resistance value R1c of the first circuit 45 is rendered higher than a value of the internal resistance of the oxygen pump cell 14 when the gas sensor 2 is in the activated state (when the internal resistance of each of the cells is equal to or lower than a reference value of 450 Ω for determining whether or not the gas sensor 2 has been activated, as described below).

Further, a second circuit 46 including a second resistor R2 and a second switch SW2 is connected between the second terminal T2 and the third terminal T3. The second resistance value R2r of the second resistor R2 is 1 kΩ. The second switch SW2 either connects the second terminal T2 and the third terminal T3 via the second resistor R2, or breaks the connection. Notably, the resistance value (on resistance) of the second switch SW2 is negligibly low as compared with the second resistance value R2r. As in the case of the first circuit 45, in the present embodiment, the resistance value R2c of the second circuit 46 (the value of the circuit resistance of the second circuit 46)=the second resistance value R2r=1 kΩ. The second circuit 46 having this resistance value R2c (=the second resistance value R2r) disconnectably connects the second terminal T2 and the third terminal T3. Notably, the resistance value R2c (=the second resistance value R2r) of the second circuit 46 is rendered lower than a value (1 MΩ or higher) of the input resistance of the A/D converter 43 for detecting the third terminal potential V3 and lower than a value (100 kΩ or higher) of the internal resistance of the oxygen concentration detection cell 24 in a state in which the oxygen concentration detection cell 24 does not exhibit oxygen ion conductivity. Meanwhile, the resistance value R2c of the second circuit 46 is rendered higher than a value (equal to or lower than 450 Ω) of the internal resistance of the oxygen concentration detection cell 24 when the gas sensor 2 is in an activated state.

The first circuit 45 and the second circuit 46 are used for diagnosing short anomaly of the gas sensor 2. As described below, when a short anomaly of the gas sensor 2 is diagnosed, the first switch SW1 and the second switch SW2 are turned on, whereby the first circuit 45 and the second circuit 46 are connected. Meanwhile, during normal use of the gas sensor 2, the first switch SW1 and the second switch SW2 are turned off.

The output of a D/A converter (hereinafter referred to as a "current DAC") 47 is connected to the first terminal T1 through a third switch SW3. The current DAC 47 serves as a pump current output circuit which supplies the pump current Ip to the oxygen pump cell 14 in accordance with an instruction from the processor 30. The third switch SW3 allows the pump current Ip from the current DAC 47 to flow to the oxygen pump cell 14 via the first terminal T1 or stops the flow of the pump current Ip.

The output of an operational amplifier 44 is connected to the second terminal T2 through a fourth switch SW4. The operational amplifier 44 serves as a reference potential circuit which outputs a reference potential Vref of +2.5 V. The fourth switch SW4 allows and stops application of the reference potential Vref from the operational amplifier 44 to the second terminal T2.

The output of a D/A converter (current DAC) 48 is connected to the third terminal T3 through a fifth switch SW5. The current DAC 48 serves as a detection cell current output circuit which supplies a detection cell current (fixed minute current Icp (for example, 10 to 20 μA) or current for detecting the internal resistance) to the oxygen concentration detection cell 24 in accordance with an instruction from the processor 30. The fifth switch SW5 allows the detection cell current (the minute current Icp, etc.) from the current DAC 48 to flow to the oxygen concentration detection cell 24 via the third terminal T3 or stops the flow of the detection cell current.

Notably, although the third switch SW3 through the fifth switch SW5 are turned on during normal use of the gas sensor 2, the third switch SW3 through the fifth switch SW5 are turned off after initial setting or when a short anomaly of the gas sensor 2 is detected. However, as described below, when diagnosis of a short anomaly of the gas sensor 2 is performed, the third switch SW3 and the fifth switch SW5 are turned off and the fourth switch SW4 is turned on.

The minute current Icp supplied to the oxygen concentration detection cell 24 forces the oxygen concentration detection cell 24 to pump the oxygen within the measurement chamber 20 to the first detection electrode 28 (porous electrode). As a result, the reference oxygen chamber 26 functions as an internal oxygen reference source.

While supplying such a fixed minute current Icp to the oxygen concentration detection cell 24, the processor 30 performs so-called digital PID control; i.e., controls the pump current Ip supplied to the oxygen pump cell 14 such that a detection cell voltage Vs generated between the opposite ends of the oxygen concentration detection cell 24 (the difference between the third terminal potential V3 detected by the A/D converter 43 and the second terminal potential V2 detected by the A/D converter 42) becomes a predetermined voltage. As a result, oxygen contained in the exhaust gas EG introduced into the measurement chamber 20 through the porous layer 18 is pumped out and oxygen is pumped into the measurement chamber 20.

The magnitude and direction of the pump current Ip supplied to the oxygen pump cell 14 and controlled by the PID control of the processor 30 change depending on the concentration of oxygen (air-fuel ratio) in the exhaust gas EG introduced into the measurement chamber 20 through the porous layer 18. As a result, the concentration of oxygen in the exhaust gas EG can be detected based on the pump current Ip. Namely, the sensor control section 40 drives and controls the gas sensor 2 by feedback-controlling the pump current Ip supplied to the oxygen pump cell 14 such that the detection cell voltage Vs generated at the oxygen concentration detection cell 24 becomes a predetermined voltage.

Also, the sensor control section 40 has a fourth terminal T4 and a fifth terminal T5 connected to the heater section control circuit 70. These fourth and fifth terminals T4 and T5 are connected to the heater section 80 of the gas sensor 2 through a fourth wiring line L4 and a fifth wiring line L5. The heater section control circuit 70 is connected to the processor 30, and the supply of electric current to the heater section 80 is controlled through PWM (pulse width modulation) control in accordance with an instruction from the processor 30.

The details of the digital PID control of the pump current Ip and the PWM control of the heater section 80 performed by the processor 30 are well known to those of ordinary skill in this field of art.

As described above, the sensor control section 40 of the gas sensor system 1 includes not only the A/D converters 41, 42, and 43 for detecting the first terminal potential V1, the second terminal potential V2, and the third terminal potential V3, but also the first circuit 45 and the second circuit 46. By using these, the sensor control section 40 can diagnose a short anomaly for some of the first wiring line L1 through the fifth wiring line L5 connected to the gas sensor 2; i.e., the first wiring line L1 which connects the Ip+ terminal of the sensor element section 3 and the first terminal T1, the second wiring line L2 which connects the COM terminal of the sensor element section 3 and the second terminal T2, and the third wiring line L3 which connects the Vs+ terminal of the sensor element section 3 and the third terminal T3.

Next, a method of diagnosing a short anomaly of the gas sensor 2 by the sensor control section 40 will be described with reference to FIG. 2 and the flowcharts of FIGS. 4 through 12 which show the processing operation of the processor 30.

First, a method for diagnosing a short anomaly before the temperature of the gas sensor 2 rises (when the temperature is low) will be described with reference to FIG. 4.

Figure 4:
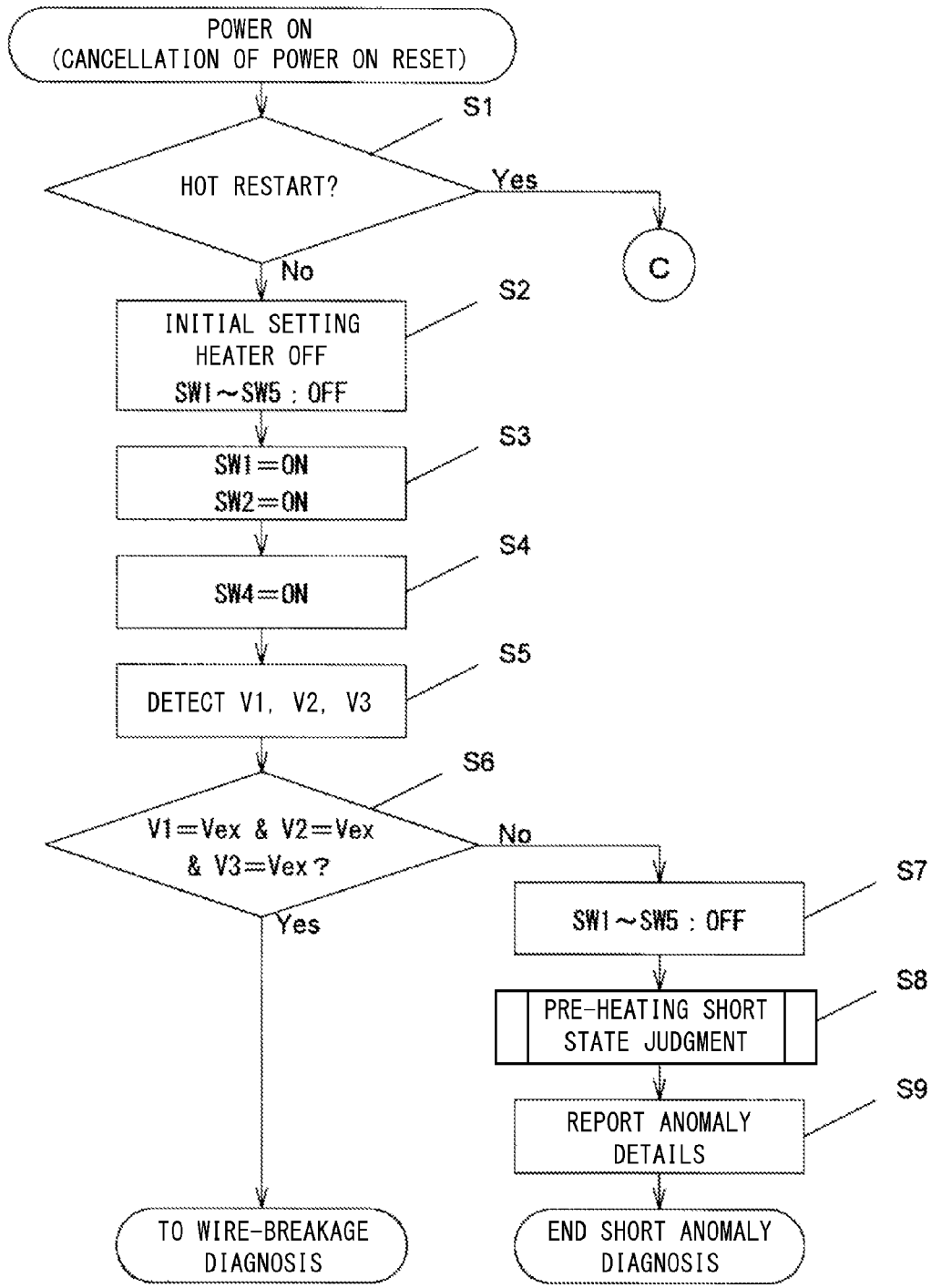
FIG. 4 is a flowchart mainly showing a processing operation of a digital signal processor of the gas sensor system according to the embodiment performed before the temperature of the gas sensor rises (when the temperature is low).

As shown in FIG. 4, when the gas sensor system 1 is powered and the power-on reset of the processor 30 is cancelled, in step S1 immediately after startup of the system 1, the processor 30 judges whether or not the startup of the system 1 is a hot restart. Notably, the hot restart refers to a case where the system 1 is started in a state in which the temperature of the gas sensor 2 is high. Specifically, in step S1, the processor 30 refers to the history of use of the system 1, and judges that the startup is a hot restart when the time between the previous stoppage of the engine ENG and the restart of the engine ENG is shorter than a predetermined time.

In the case where the processor 30 judges in step S1 that the startup is not a hot restart (No); namely, in the case where the gas sensor 2 is in a state in which its temperature is lower than that in the activated state (for example, before the temperature of the gas sensor 2 rises) (specifically, a state in which the temperature of the gas sensor 2 is lower than a judgment temperature for judging whether or not the gas sensor 2 has been activated (hereinafter referred to as a "low-temperature state")), the processor 30 proceeds to step S2. Meanwhile, in the case where the processor 30 judges that the startup is a hot restart (Yes); namely, in the case where the temperature of the gas sensor 2 is high (includes the activated state), the processor 30 proceeds to step S11 of FIG. 8 described below.

Notably, in the present embodiment, the reference resistance value for the internal resistances of the cell used for judging whether or not the gas sensor 2 has been activated is set to 450 Ω. Namely, when after diagnosis of a short anomaly, the internal resistances of the oxygen pump cell 14 and the oxygen concentration detection cell 24 become lower than 450 Ω in the course of raising the temperature of the gas sensor 2, the processor 30 judges that the gas sensor 2 has been activated. Accordingly, when the temperature of the gas sensor 2 falls within a temperature range within which the internal resistances of the oxygen pump cell 14 and the oxygen concentration detection cell 24 are lower than 450 Ω, the gas sensor 2 is in the activated state.

In the present embodiment, the temperature range of the low-temperature state which is lower than that in the activated state is set to a temperature range within which the internal resistances of the oxygen pump cell 14 and the oxygen concentration detection cell 24 of the gas sensor 2 become higher than 1 kΩ (>450 Ω). Therefore, a period of time required for the temperature of the gas sensor 2 to decrease from the temperature during operation to a temperature at which the internal resistance of each cell becomes higher than 1 k☐ is defined as the above-described predetermined time, and when the time between the previous stoppage of the engine ENG and the restart of the engine ENG is shorter than the predetermined time, the startup is a hot restart.

In step S2, the processor 30 performs initial setting, turns off the supply of electric current to the heater section 80, and turns off all the first through fifth switches SW1-SW5.

Next, in step S3, the processor 30 turns on the first switch SW1 and the second switch SW2 to thereby connect the first circuit 45 and the second circuit 46. As a result, the first resistor R1 whose first resistance value R1r is 1 kΩ (the first circuit 45 whose resistance value R1c is 1 kΩ) is connected between the first terminal T1 and the second terminal T2 in parallel with the oxygen pump cell 14, and the second resistor R2 whose second resistance value R2r is 1 kΩ (the second circuit 46 whose resistance value R2c is 1 kΩ) is connected between the second terminal T2 and the third terminal T3 in parallel with the oxygen concentration detection cell 24. Therefore, when the gas sensor 2 is in the low-temperature state; namely, when the internal resistances of the oxygen pump cell 14 and the oxygen concentration detection cell 24 are higher than 1 kΩ, each of the resistance between the first terminal T1 and the second terminal T2 and the resistance between the second terminal T2 and the third terminal T3 becomes about 500Ω to about 1 kΩ.

In step S4 subsequent to step S3, the processor 30 turns on the fourth switch SW4. As a result, the reference potential Vref of +2.5 V is applied from the operational amplifier 44 to the second terminal T2 as an examination potential Vex (the examination potential Vex=+2.5 V (=the reference potential Vref)). Therefore, if a short is not present on the first wiring line L1 through the third wiring line L3, each of the first terminal potential V1 of the first terminal T1, the second terminal potential V2 of the second terminal T2, and the third terminal potential V3 of the third terminal T3 becomes equal to the examination potential Vex. In the case where one of the first wiring line L1 through the third wiring line L3 is shorted to the ground potential GND or the power supply potential (the battery potential VB), at least one of the first terminal potential V1 through the third terminal potential V3 deviates from the examination potential Vex and becomes a potential (≅the ground potential GND) lower than the examination potential Vex or a potential (≅the battery potential VB) higher than the examination potential Vex.

Next, in step S5, the processor 30 detects the first terminal potential V1, the second terminal potential V2, and the third terminal potential V3 using the A/D converters 41, 42, and 43 in a state in which the gas sensor 2 is in the low-temperature state.

In step S6 subsequent thereto, the processor 30 judges whether or not all the first terminal potential V1, the second terminal potential V2, and the third terminal potential V3 detected in step S5 are equal to the examination potential Vex.

In the case where all the first terminal potential V1, the second terminal potential V2, and the third terminal potential V3 are equal to the examination potential Vex (Yes), the processor 30 judges that the gas sensor 2 has no short anomaly and proceeds to wire-breakage diagnosis processing to be performed after the short anomaly diagnosis processing. Notably, the details of the wire-breakage diagnosis processing are not described herein.

Meanwhile, in the case where at least one of the first terminal potential V1, the second terminal potential V2, the third terminal potential V3 is not equal to the examination potential Vex (No), the processor 30 judges that the gas sensor 2 has a short anomaly and proceeds to step S7.

In step S7, the processor 30 turns off all the first through fifth switches SW1-SW5 again. Next, the processor 30 proceeds to step S8 so as to execute a pre-heating short state judgment routine (which will be described next) shown in FIGS. 5 through 7. Notably, in this pre-heating short state judgment routine, the processor 30 determines the location where the short anomaly has occurred and the source (end) of the short-circuit (short state) based on the first terminal potential V1, the second terminal potential V2, and the third terminal potential V3 detected in step S5 and used for the judgment in step S6.

Upon completing execution of the pre-heating short state judgment routine, in step S9, the processor 30 reports the details of the anomaly to the ECU 100, and ends the processing for detecting a short anomaly.

Next, the pre-heating short state judgment routine shown in FIGS. 5 through 7 will be described.

Figure 5:
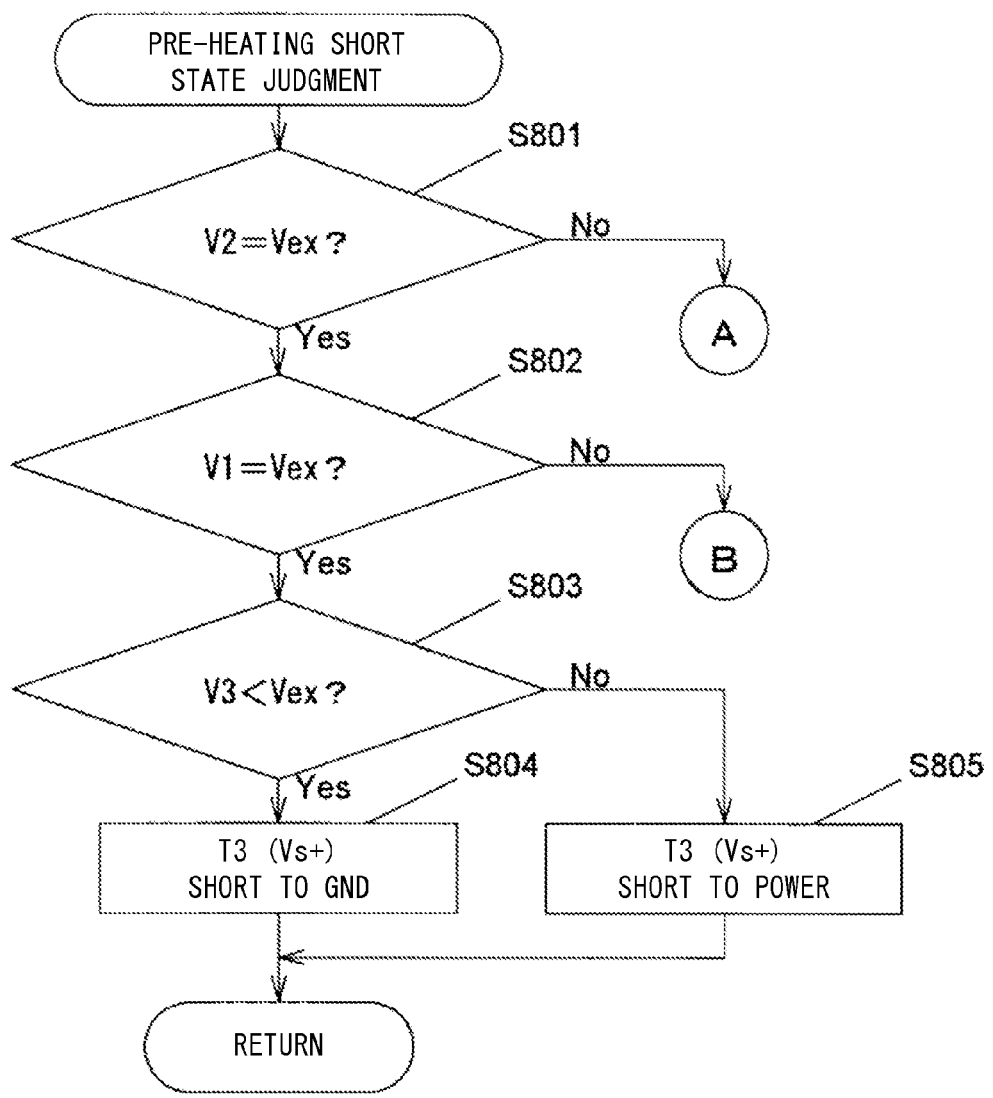
FIG. 5 is a first flowchart showing an operation of the digital signal processor of the gas sensor system according to the embodiment for executing a pre-heating short state judgment routine.

When the processor 30 starts the pre-heating short state judgment routine, in step S801 shown in FIG. 5, the processor 30 judges whether or not the second terminal potential V2 used for the judgment in step S6 is equal to the examination potential Vex. In the case where the second terminal potential V2 is equal to the examination potential Vex (Yes), the processor 30 proceeds to step S802. In the case where the second terminal potential V2 is not equal to the examination potential Vex (No), the processor 30 proceeds to step S806 shown in FIG. 6.

In step S802, the processor 30 judges whether or not the first terminal potential V1 used for the judgment in step S6 is equal to the examination potential Vex. In the case where the first terminal potential V1 is equal to the examination potential Vex (Yes), the processor 30 proceeds to step S803. In the case where the first terminal potential V1 is not equal to the examination potential Vex (No), the processor 30 proceeds to step S814 shown in FIG. 7.

In step S803, the processor 30 judges whether or not the third terminal potential V3 used for the judgment in step S6 is lower than the examination potential Vex. In the case where the processor 30 judges in step S803 that the third terminal potential V3 is lower than the examination potential Vex (Yes), the processor 30 proceeds to step S804. In the other case (No), the processor 30 proceeds to step S805.

Notably, before the point when the processor 30 proceeds to step S803, the processor 30 has already judged that both the first terminal potential V1 and the second terminal potential V2 used for the determination in step S6 are equal to the examination potential Vex (steps S801 and S802). Also, the processor 30 has already judged that at least one of the first terminal potential V1, the second terminal potential V2, and the third terminal potential V3 is not equal to the examination potential Vex (step S6). Therefore, before the point when the processor 30 proceeds to step S803, it has already been determined that the third terminal potential V3 is not equal to the examination potential Vex. Therefore, the case where the result of the judgment in step S803 becomes No and the processor 30 proceeds to step S805 corresponds to the case where the third terminal potential V3 is higher than the examination potential Vex.

In the case where the processor 30 judges through the above-described steps that the first terminal potential V1 and the second terminal potential V2 are equal to the examination potential Vex and the third terminal potential V3 is lower than the examination potential Vex, the processor 30 proceeds to step S804. In step S804, the processor 30 judges that the third wiring line L3 connected to the third terminal T3 is shorted to the ground potential GND (third short-to-GND state), and determines the details of the anomaly to be reported to the ECU 100.

In the case where the first terminal potential V1 and the second terminal potential V2 are equal to the examination potential Vex and the third terminal potential V3 is higher than the examination potential Vex, the processor 30 proceeds to step S805. In step S805, the processor 30 judges that the third wiring line L3 connected to the third terminal T3 is shorted to the power supply potential (battery potential VB) (third short-to-power state) (determines the details of the anomaly).

In both the case where the processor 30 proceeds to step S804 and the case where the processor 30 proceeds to step S805, the processor 30 ends the pre-heating short state judgment routine and proceeds to step S9 shown in FIG. 4.

Next, step S806 shown in FIG. 6 and steps subsequent thereto will be described.

Before the point when the processor 30 proceeds to step S806, the processor 30 has already judged in step S801 that the second terminal potential V2 is not equal to the examination potential Vex.

In step S806, the processor 30 judges whether or not the second terminal potential V2 is lower than the examination potential Vex. In the case where the second terminal potential V2 is lower than the examination potential Vex (Yes), the processor 30 proceeds to step S807. In the other case (No); i.e., the case where the second terminal potential V2 is higher than the examination potential Vex, the processor 30 proceeds to step S810.

In step S807, the processor 30 judges whether or not the first terminal potential V1 is lower than the examination potential Vex. In the case where the first terminal potential V1 is lower than the examination potential Vex (Yes), the processor 30 proceeds to step S808. In the other case (No), the processor 30 proceeds to step S813.

In step S808, the processor 30 judges whether or not the third terminal potential V3 is lower than the examination potential Vex. In the case where the third terminal potential V3 is lower than the examination potential Vex (Yes), the processor 30 proceeds to step S809. In the other case (No), the processor 30 proceeds to step S813.

In step S810, the processor 30 judges whether or not the first terminal potential V1 is higher than the examination potential Vex. In the case where the first terminal potential V1 is higher than the examination potential Vex (Yes), the processor 30 proceeds to step S811. In the other case (No), the processor 30 proceeds to step S813.

In step S811, the processor 30 judges whether or not the third terminal potential V3 is higher than the examination potential Vex. In the case where the third terminal potential V3 is higher than the examination potential Vex (Yes), the processor 30 proceeds to step S812. In the other case (No), the processor 30 proceeds to step S813.

In the case where the processor 30 judges through the above-described steps that all of the first terminal potential V1, the second terminal potential V2, and the third terminal potential V3 are lower than the examination potential Vex, the processor 30 proceeds to step S809 and judges that the second wiring line L2 connected to the second terminal T2 is shorted to the ground potential GND (second short-to-GND state) (determines the details of the anomaly).

In the case where all of the first terminal potential V1, the second terminal potential V2, and the third terminal potential V3 are higher than the examination potential Vex, the processor 30 proceeds to step S812 and judges that the second wiring line L2 connected to the second terminal T2 is shorted to the power supply potential (battery potential VB) (second short-to-power state) (determines the details of the anomaly).

In the case where the second terminal potential V2 is not equal to the examination potential Vex and the above-described judgment criteria are not satisfied, the processor 30 proceeds to step S813 and judges that the anomaly is one of other types of anomalies (determines the details of the anomaly).

Subsequently, in all of the cases where the processor 30 proceeds to step S809, the case where the processor 30 proceeds to step S812, and the case where the processor 30 proceeds to step S813, the processor 30 ends the pre-heating short state judgment routine and proceeds to step S9 shown in FIG. 4.

Next, step S814 shown in FIG. 7 and steps subsequent thereto will be described.

Before the point when the processor 30 proceeds to step S814, the processor 30 has already judged in steps S801 and S802 that the second terminal potential V2 is equal to the examination potential Vex and the first terminal potential V1 is not equal to the examination potential Vex.

In step S814, the processor 30 judges whether or not the third terminal potential V3 is equal to the examination potential Vex. In the case where the third terminal potential V3 is equal to the examination potential Vex (Yes), the processor 30 proceeds to step S815. In the other case (No), the processor 30 proceeds to step S818.

In step S815, the processor 30 judges whether or not the first terminal potential V1, which has already been judged in step S802 not to be equal to the examination potential Vex, is lower than the examination potential Vex. In the case where the first terminal potential V1 is lower than the examination potential Vex (Yes), the processor 30 proceeds to step S816. In the other case (No); namely, in the case where the first terminal potential V1 is higher than the examination potential Vex, the processor 30 proceeds to step S817.

In the case where the processor 30 judges through the above-described steps that the second terminal potential V2 and the third terminal potential V3 are equal to the examination potential Vex and the first terminal potential V1 is lower than the examination potential Vex, the processor 30 proceeds to step S816 and judges that the first wiring line L1 connected to the first terminal T1 is shorted to the ground potential GND (first short-to-GND state) (determines the details of the anomaly).

In the case where the second terminal potential V2 and the third terminal potential V3 are equal to the examination potential Vex and the first terminal potential V1 is higher than the examination potential Vex, the processor 30 proceeds to step S817 and judges that the first wiring line L1 connected to the first terminal T1 is shorted to the power supply potential (battery potential VB) (first short-to-power state) (determines the details of the anomaly).

In the case where the second terminal potential V2 is equal to the examination potential Vex and the first terminal potential V1 and the third terminal potential V3 are not equal to the examination potential Vex, the processor 30 proceeds to step S818 and judges that the anomaly is one of other types of anomalies (determines the details of the anomaly).

Subsequently, in all of the cases where the processor 30 proceeds to step S816, the case where the processor 30 proceeds to step S817, and the case where the processor 30 proceeds to step S818, the processor 30 ends the pre-heating short state judgment routine and proceeds to step S9 shown in FIG. 4.

Figure 6:
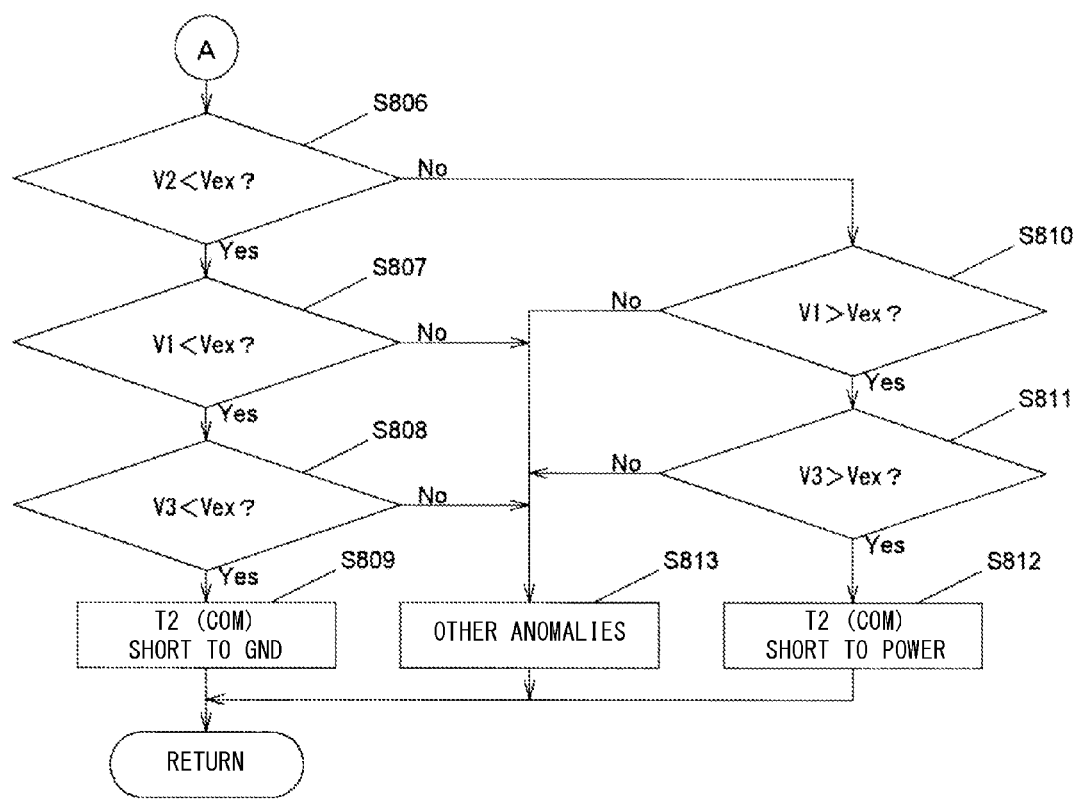
FIG. 6 is a second flowchart showing operation of the digital signal processor of the gas sensor system according to the embodiment for executing the pre-heating short state judgment routine.
Figure 7:
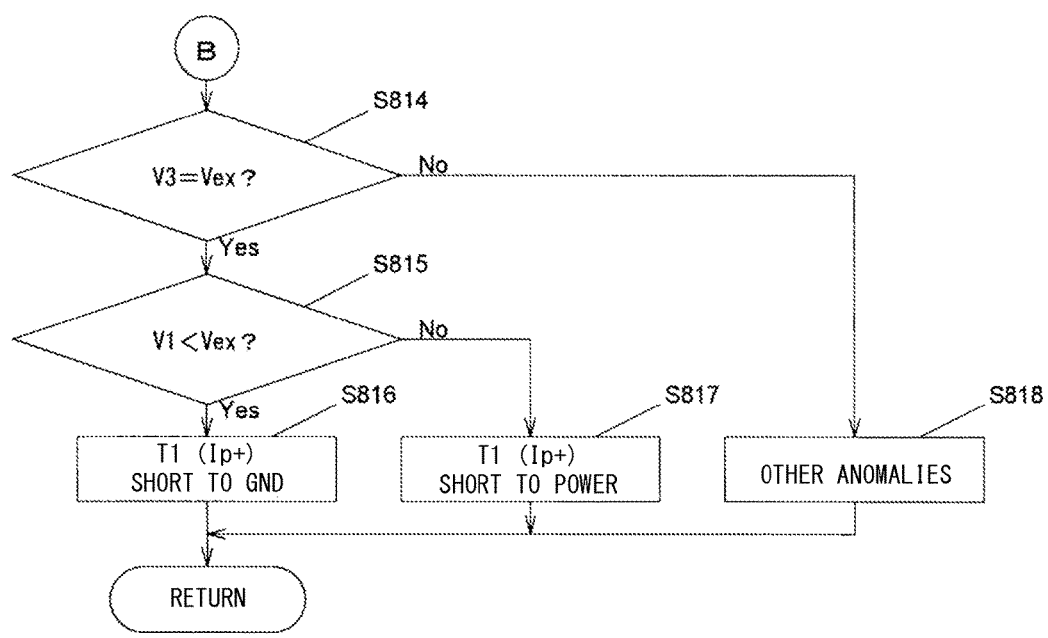
FIG. 7 is a third flowchart showing operation of the digital signal processor of the gas sensor system according to the embodiment for executing the pre-heating short state judgment routine.

By the pre-heating short state judgment routine shown in FIGS. 5 through 7, the processor 30 can judge, before the temperature of the gas sensor 2 rises (when the temperature is low), six types of states in total, including three types of short-to-GND states (the first short-to-GND state, the second short-to-GND state, and the third short-to-GND state) and three types of short-to-power states (the first short-to-power state, the second short-to-power state, and the third short-to-power state) as well as other anomalies, based on the first terminal potential V1, the second terminal potential V2, and the third terminal potential V3 detected in step S15.

Next, a method for diagnosing a short anomaly when the temperature of the gas sensor 2 is high will be described with reference to FIGS. 8 and 9.

Figure 8:
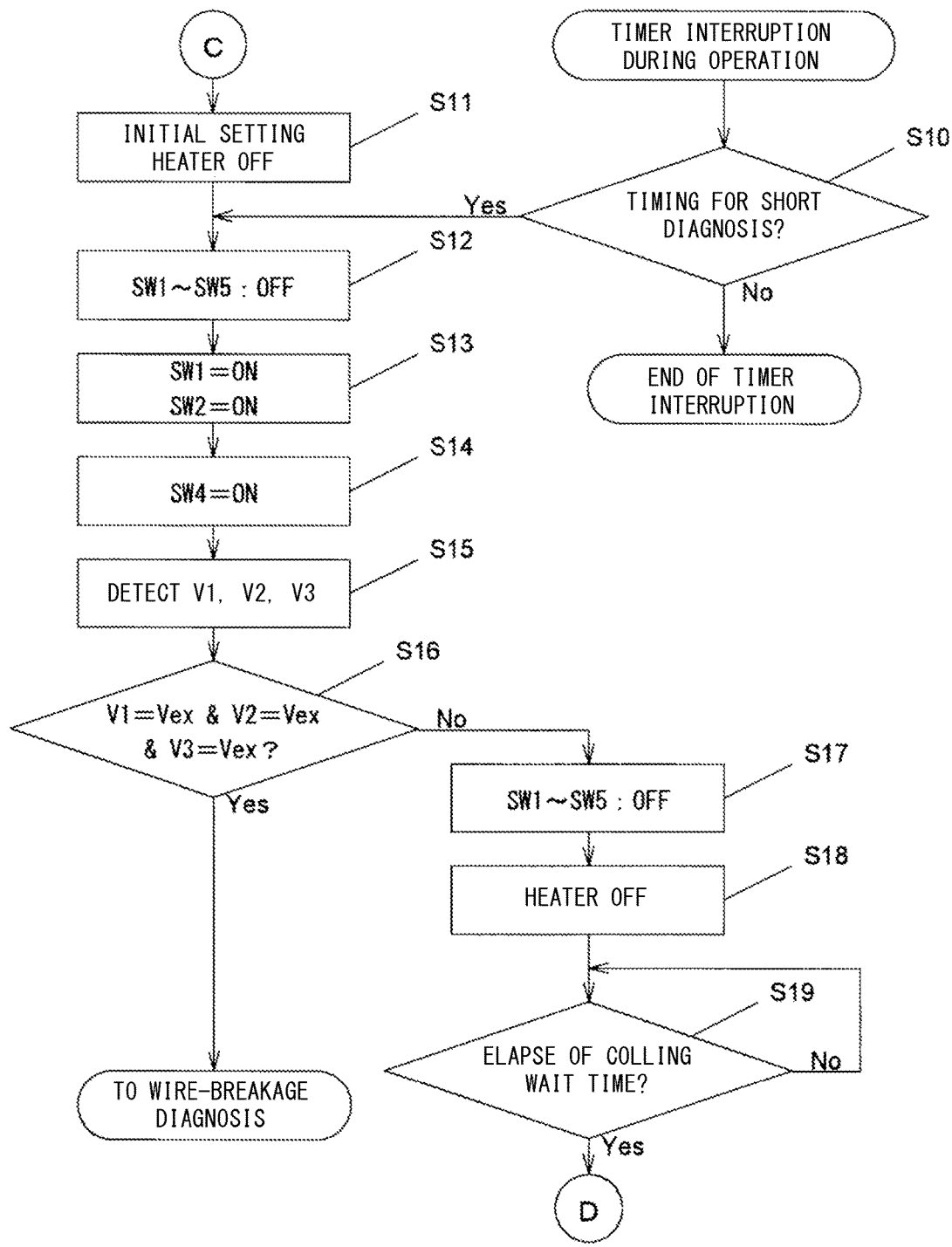
FIG. 8 is a flowchart mainly showing a processing operation of the digital signal processor of the gas sensor system according to the embodiment performed when the temperature of the gas sensor is high.
Figure 9:
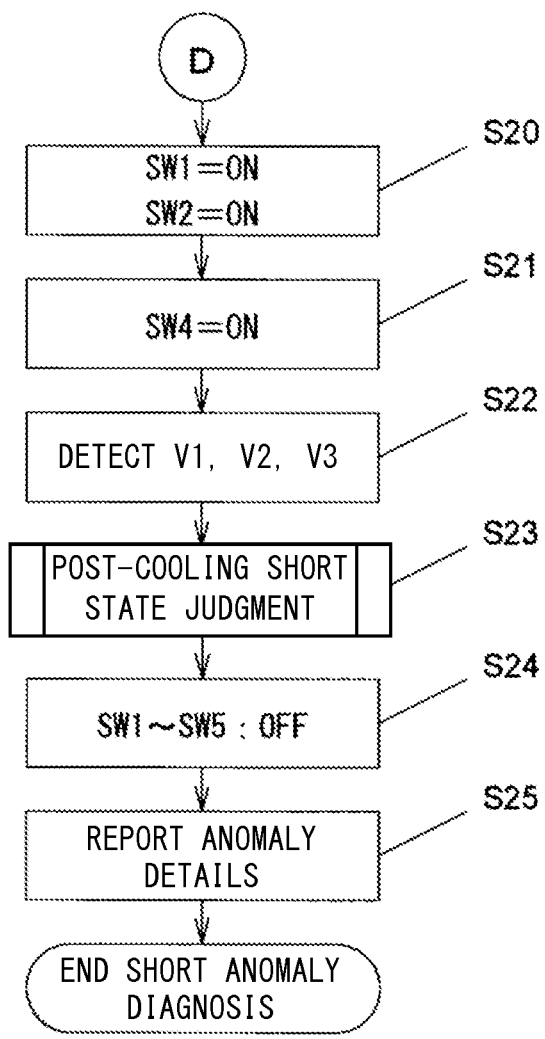
FIG. 9 is a flowchart showing a processing operation of the digital signal processor of the gas sensor system according to the embodiment performed after the gas sensor is cooled.

In the case where, as described above, the power-on reset of the processor 30 is cancelled and the startup is judged to be a hot restart in step S1 shown in FIG. 4 (Yes); i.e., in the case where the temperature of the gas sensor 2 is high, the processor 30 proceeds to step S11 shown in FIG. 8.

In step S11, the processor 30 performs an initial setting, cuts-off the supply of electric current to the heater section 80, and then proceeds to step S12.

In the present gas sensor system 1, in order to diagnose a short anomaly in a period during which the gas sensor 2 is operating after the temperature of the gas sensor 2 has reached a high temperature, a timer interruption is generated, and the processor 30 judges in step S10 whether or not the present timing is a short anomaly diagnosis timing for diagnosing the short anomaly of the gas sensor 2 while the gas sensor 2 is operating. In the case where the processor 30 judges in step S10 that the present timing is a short anomaly diagnosis timing (Yes), the processor 30 proceeds to step S12. Meanwhile, in the case where the processor 30 judges that the present timing is not the short anomaly diagnosis timing (No), the processor 30 stops the timer interruption. As a result, even in the period during which the gas sensor 2 is operating, diagnosis of a short anomaly is performed periodically.

In step S12, the processor 30 turns off all of the first through fifth switches SW1-SW5.

Next, in step S13, the processor 30 turns on the first switch SW1 and the second switch SW2 to thereby connect the first circuit 45 and the second circuit 46. As a result, the first resistor R1 whose first resistance value R1r is 1 kΩ (the first circuit 45 whose resistance value R1c is 1 kΩ) is connected between the first terminal T1 and the second terminal T2 in parallel with the oxygen pump cell 14, and the second resistor R2 whose second resistance value R2r is 1 kΩ (the second circuit 46 whose resistance value R2c is 1 kΩ) is connected between the second terminal T2 and the third terminal T3 in parallel with the oxygen concentration detection cell 24. In the case where the temperature of the gas sensor 2 is high, the internal resistances of the oxygen pump cell 14 and the oxygen concentration detection cell 24 are each lower than 1 kΩ. In particular, in the case where the time between the previous stoppage of the engine ENG and the restart of the engine ENG is short, the internal resistances are sufficiently lower than 1 kΩ (specifically, 100Ω or lower). Therefore, the resistance between the first terminal T1 and the second terminal T2 is approximately equal to the internal resistance of the oxygen pump cell 14, and the resistance between the second terminal T2 and the third terminal T3 is approximately equal to the internal resistance of the oxygen concentration detection cell 24.

In step S14 subsequent to step S13, the processor 30 turns on the fourth switch SW4. As a result, the reference potential Vref of +2.5 V is applied to the second terminal T2 as an examination potential Vex. Therefore, if a short is not present on the first wiring line L1 through the third wiring line L3, each of the first terminal potential V1 of the first terminal T1, the second terminal potential V2 of the second terminal T2, and the third terminal potential V3 of the third terminal T3 becomes equal to the examination potential Vex. In the case where one of the first wiring line L1 through the third wiring line L3 is shorted to the ground potential GND or the power supply potential (the battery potential VB), at least one of the first terminal potential V1 through the third terminal potential V3 deviates from the examination potential Vex and becomes a potential (≅the ground potential GND) lower than the examination potential Vex or a potential (≅the battery potential VB) higher than the examination potential Vex.

Next, in step S15, the processor 30 detects the first terminal potential V1, the second terminal potential V2, and the third terminal potential V3 using the A/D converters 41, 42, and 43 in a state in which the temperature of the gas sensor 2 is high.

In step S16 subsequent thereto, the processor 30 judges whether or not all of the first terminal potential V1, the second terminal potential V2, and the third terminal potential V3 detected in step S15 are equal to the examination potential Vex.

In the case where the temperature of the gas sensor 2 is high; namely, in the case where the internal resistances of the oxygen pump cell 14 and the oxygen concentration detection cell 24 are low, the potential of a terminal where a short has occurred becomes approximately equal to the potential of another terminal where no short is present in some cases. However, even in the case where the temperature of the gas sensor 2 is high, when at least one of the first terminal potential V1 through the third terminal potential V3 is not equal to the examination potential Vex, the gas sensor 2 is found to have a short anomaly.

Therefore, in the case where the processor 30 judges in step S16 that all the first terminal potential V1, the second terminal potential V2, and the third terminal potential V3 are equal to the examination potential Vex (Yes), the processor 30 judges that the gas sensor 2 has no short anomaly and proceeds to the wire-breakage diagnosis processing to be performed after this short anomaly diagnosis processing, as in the case where the gas sensor 2 is in the low temperature state.

Meanwhile, in the case where at least one of the first terminal potential V1, the second terminal potential V2, the third terminal potential V3 is not equal to the examination potential Vex (No), the processor 30 judges that the gas sensor 2 has a short anomaly and proceeds to step S17.

In step S17, the processor 30 turns off all of the first through fifth switches SW1-SW5 again. Next, the processor 30 proceeds to step S18 and stops the supply of electric current to the heater section 80. In the case of a hot restart, the supply of electric current to the heater section 80 has already been cut-off in step S11. However, in the case where the short anomaly diagnosis timing comes while the gas sensor 2 is operating, the supply of electric-current to the heater section 80 is stopped in the step S17.

Next, the processor 30 proceeds to step S19 so as to judge whether or not a predetermined cooling wait time (for example, 60 seconds) has elapsed. In the case where the cooling wait time has not elapsed (No), the processor 30 waits for cooling of the gas sensor 2 by repeating step S19. When the processor 30 determines in step S19 that the cooling wait time has elapsed (Yes), the processor 30 proceeds step S20 shown in FIG. 9.

In steps S20 through S22, after cooling the gas sensor 2, the processor 30 turns on the first switch SW1 and the second switch SW2, then turns on the fourth switch SW4, and newly detects the first terminal potential V1, the second terminal potential V2, the third terminal potential V3 using the A/D converters 41, 42, and 43 in the same manner as in steps S13 through S15.

Next, the processor 30 proceeds to step S23 so as to execute a post-cooling short state judgment routine (which will be described next) shown in FIGS. 10 through 12. Notably, in this post-cooling short state judgment routine, the processor 30 determines the location of the short anomaly and the source (end) of the short-circuit (short state) based on the first terminal potential V1, the second terminal potential V2, and the third terminal potential V3 newly detected in step S22.

Upon completing execution of the post-cooling short state judgment routine, in step S24, the processor 30 turns off all of the first switch SW1 through the fifth switch SW5 again. Subsequently, in step S25, the processor 30 reports the details of the anomaly to the ECU 100, and ends the processing for detecting a short anomaly.

Next, the post-cooling short state judgment routine shown in FIGS. 10 through 12 will be described.

Figure 10:
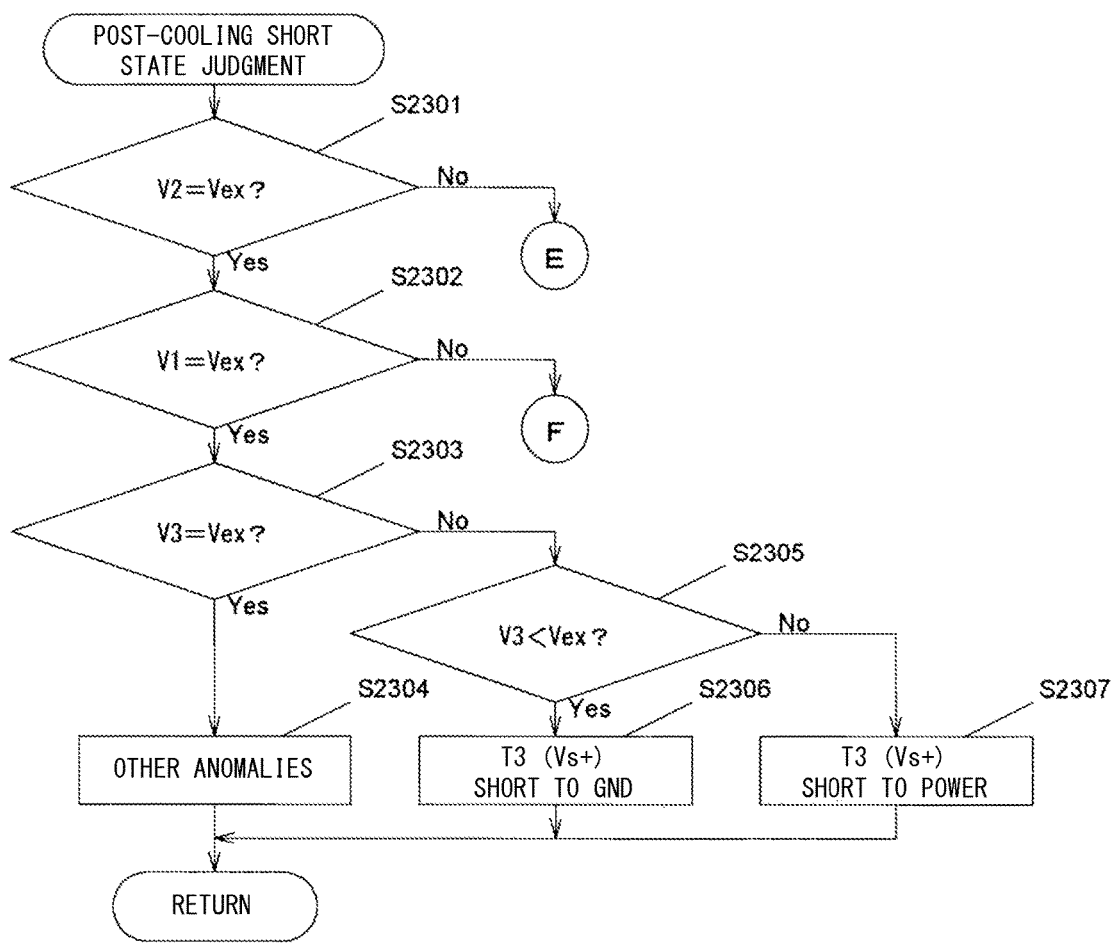
FIG. 10 is a first flowchart showing an operation of the digital signal processor of the gas sensor system according to the embodiment for executing a post-cooling short state judgment routine.

When the processor 30 starts the post-cooling short state judgment routine, in step S2301 shown in FIG. 10, the processor 30 first judges whether or not the second terminal potential V2 newly detected in step S22 is equal to the examination potential Vex. In the case where the second terminal potential V2 is equal to the examination potential Vex (Yes), the processor 30 proceeds to step S2302. In the case where the second terminal potential V2 is not equal to the examination potential Vex (No), the processor 30 proceeds to step S2308 shown in FIG. 11.

In step S2302, the processor 30 judges whether or not the first terminal potential V1 newly detected in step S22 is equal to the examination potential Vex. In the case where the first terminal potential V1 is equal to the examination potential Vex (Yes), the processor 30 proceeds to step S2303. In the case where the first terminal potential V1 is not equal to the examination potential Vex (No), the processor 30 proceeds to step S2316 shown in FIG. 12.

In step S2303, the processor 30 judges whether or not the third terminal potential V3 newly detected in step S22 is equal to the examination potential Vex. In the case where the third terminal potential V3 is equal to the examination potential Vex (Yes), the processor 30 proceeds to step S2304. In the case where the third terminal potential V3 is not equal to the examination potential Vex (No), the processor 30 proceeds to step S2305.

In the case where the processor 30 proceeds to step S2304, this means that all of the first terminal potential V1, the second terminal potential V2, and the third terminal potential V3 newly detected in step S22 are equal to the examination potential Vex. This differs from the result of the judgment in step S16 that the gas sensor 2 has a short anomaly, which judgment was made based on the first terminal potential V1, the second terminal potential V2, and the third terminal potential V3 detected in step S15 when the temperature of the gas sensor 2 was high. Therefore, in step S2304, the processor 30 determines that the anomaly is an uncertain anomaly and handles it as one of other types of anomalies.

In step S2305, the processor 30 judges whether or not the third terminal potential V3, which has been judged not to be equal to the examination potential Vex in step S2303, is lower than the examination potential Vex. In the case where the third terminal potential V3 is lower than the examination potential Vex (Yes), the processor 30 proceeds to step S2306. In other case (No); i.e., the case where the third terminal potential V3 is higher than the examination potential Vex, the processor 30 proceeds to step S2307.

In the case where the processor 30 judges through the above-described steps that the first terminal potential V1 and the second terminal potential V2 are equal to the examination potential Vex and the third terminal potential V3 is lower than the examination potential Vex, the processor 30 proceeds to step S2306. In step S2306, the processor 30 judges that the third wiring line L3 connected to the third terminal T3 is shorted to the ground potential GND (third short-to-GND state) (determines the details of the anomaly).

In the case where the first terminal potential V1 and the second terminal potential V2 are equal to the examination potential Vex and the third terminal potential V3 is higher than the examination potential Vex, the processor 30 proceeds to step S2307. In step S2307, the processor 30 judges that the third wiring line L3 connected to the third terminal T3 is shorted to the power supply potential (battery potential VB) (third short-to-power state) (determines the details of the anomaly).

In the case where all the first terminal potential V1, the second terminal potential V2, and the third terminal potential V3 are equal to the examination potential Vex, the processor 30 proceeds to step S2304 and judges that the anomaly is one of other types of anomalies (determines the details of the anomaly).

Subsequently, in all the cases where the processor 30 proceeds to step S2304, the case where the processor 30 proceeds to step S2306, and the case where the processor 30 proceeds to step S2307, the processor 30 ends the post-cooling short state judgment routine and proceeds to step S24 shown in FIG. 9.

Next, step S2308 shown in FIG. 11 and steps subsequent thereto will be described.

Before the point when the processor 30 proceeds to step S2308, the processor 30 has already judged in step S2301 that the second terminal potential V2 is not equal to the examination potential Vex.

In step S2308, the processor 30 judges whether or not the second terminal potential V2 is lower than the examination potential Vex. In the case where the second terminal potential V2 is lower than the examination potential Vex (Yes), the processor 30 proceeds to step S2309. In the other case (No); i.e., the case where the second terminal potential V2 is higher than the examination potential Vex, the processor 30 proceeds to step S2312.

In step S2309, the processor 30 judges whether or not the first terminal potential V1 is lower than the examination potential Vex. In the case where the first terminal potential V1 is lower than the examination potential Vex (Yes), the processor 30 proceeds to step S2310. In the other case (No), the processor 30 proceeds to step S2315.

In step S2310, the processor 30 judges whether or not the third terminal potential V3 is lower than the examination potential Vex. In the case where the third terminal potential V3 is lower than the examination potential Vex (Yes), the processor 30 proceeds to step S2311. In the other case (No), the processor 30 proceeds to step S2315.

In step S2312, the processor 30 judges whether or not the first terminal potential V1 is higher than the examination potential Vex. In the case where the first terminal potential V1 is higher than the examination potential Vex (Yes), the processor 30 proceeds to step S2313. In the other case (No), the processor 30 proceeds to step S2315.

In step S2313, the processor 30 judges whether or not the third terminal potential V3 is higher than the examination potential Vex. In the case where the third terminal potential V3 is higher than the examination potential Vex (Yes), the processor 30 proceeds to step S2314. In the other case (No), the processor 30 proceeds to step S2315.

In the case where the processor 30 judges through the above-described steps that all of the first terminal potential V1, the second terminal potential V2, and the third terminal potential V3 are lower than the examination potential Vex, the processor 30 proceeds to step S2311 and judges that the second wiring line L2 connected to the second terminal T2 is shorted to the ground potential GND (second short-to-GND state) (determines the details of the anomaly).

In the case where all of the first terminal potential V1, the second terminal potential V2, and the third terminal potential V3 are higher than the examination potential Vex, the processor 30 proceeds to step S2314 and judges that the second wiring line L2 connected to the second terminal T2 is shorted to the power supply potential (battery potential VB) (second short-to-power state) (determines the details of the anomaly).

In the case where the second terminal potential V2 is not equal to the examination potential Vex and the above-described judgment criteria are not satisfied, the processor 30 proceeds to step S2315 and judges that the anomaly is one of other types of anomalies (determines the details of the anomaly).

Subsequently, in all the cases where the processor 30 proceeds to step S2311, the case where the processor 30 proceeds to step S2314, and the case where the processor 30 proceeds to step S2315, the processor 30 ends the post-cooling short state judgment routine and proceeds to step S24 shown in FIG. 9.

Next, step S2316 shown in FIG. 12 and steps subsequent thereto will be described.

Before the point when the processor 30 proceeds to step S2316, the processor 30 has already judged in steps S2301 and S2302 that the second terminal potential V2 is equal to the examination potential Vex and the first terminal potential V1 is not equal to the examination potential Vex.

In step S2316, the processor 30 judges whether or not the third terminal potential V3 is equal to the examination potential Vex. In the case where the third terminal potential V3 is equal to the examination potential Vex (Yes), the processor 30 proceeds to step S2317. In the other case (No), the processor 30 proceeds to step S2320.

In step S2317, the processor 30 judges whether or not the first terminal potential V1, which has already been judged in step S2302 not to be equal to the examination potential Vex, is lower than the examination potential Vex. In the case where the first terminal potential V1 is lower than the examination potential Vex (Yes), the processor 30 proceeds to step S2318. In the other case (No); namely, in the case where the first terminal potential V1 is higher than the examination potential Vex, the processor 30 proceeds to step S2319.

In the case where the processor 30 judges through the above-described steps that the second terminal potential V2 and the third terminal potential V3 are equal to the examination potential Vex and the first terminal potential V1 is lower than the examination potential Vex, the processor 30 proceeds to step S2318 and judges that the first wiring line L1 connected to the first terminal T1 is shorted to the ground potential GND (first short-to-GND state) (determines the details of the anomaly).

In the case where the second terminal potential V2 and the third terminal potential V3 are equal to the examination potential Vex and the first terminal potential V1 is higher than the examination potential Vex, the processor 30 proceeds to step S2319 and judges that the first wiring line L1 connected to the first terminal T1 is shorted to the power supply potential (battery potential VB) (first short-to-power state) (determines the details of the anomaly).

In the case where the second terminal potential V2 is equal to the examination potential Vex and the first terminal potential V1 and the third terminal potential V3 are not equal to the examination potential Vex, the processor 30 proceeds to step S2320 and judges that the anomaly is one of other types of anomalies (determines the details of the anomaly).

Subsequently, in all of the cases where the processor 30 proceeds to step S2318, the case where the processor 30 proceeds to step S2319, and the case where the processor 30 proceeds to step S2320, the processor 30 ends the pre-heating short state judgment routine and proceeds to step S24 shown in FIG. 9.

Figure 11:
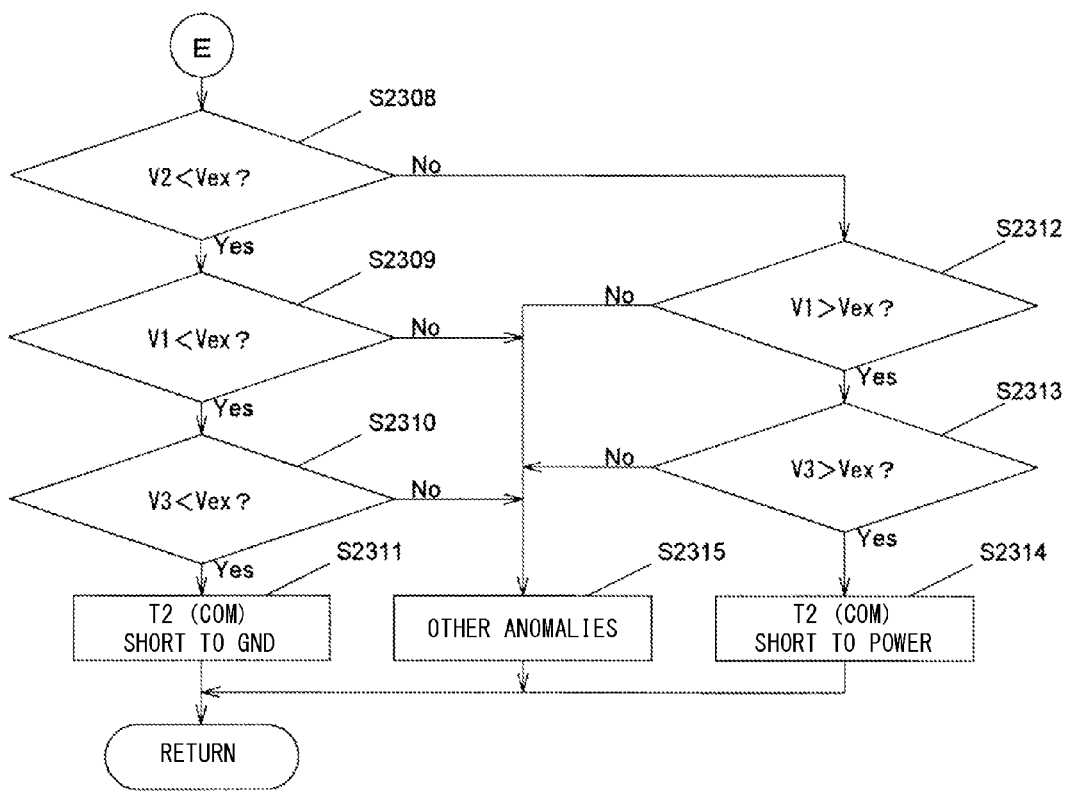
FIG. 11 is a second flowchart showing operation of the digital signal processor of the gas sensor system according to the embodiment for executing the post-cooling short state judgment routine.
Figure 12:
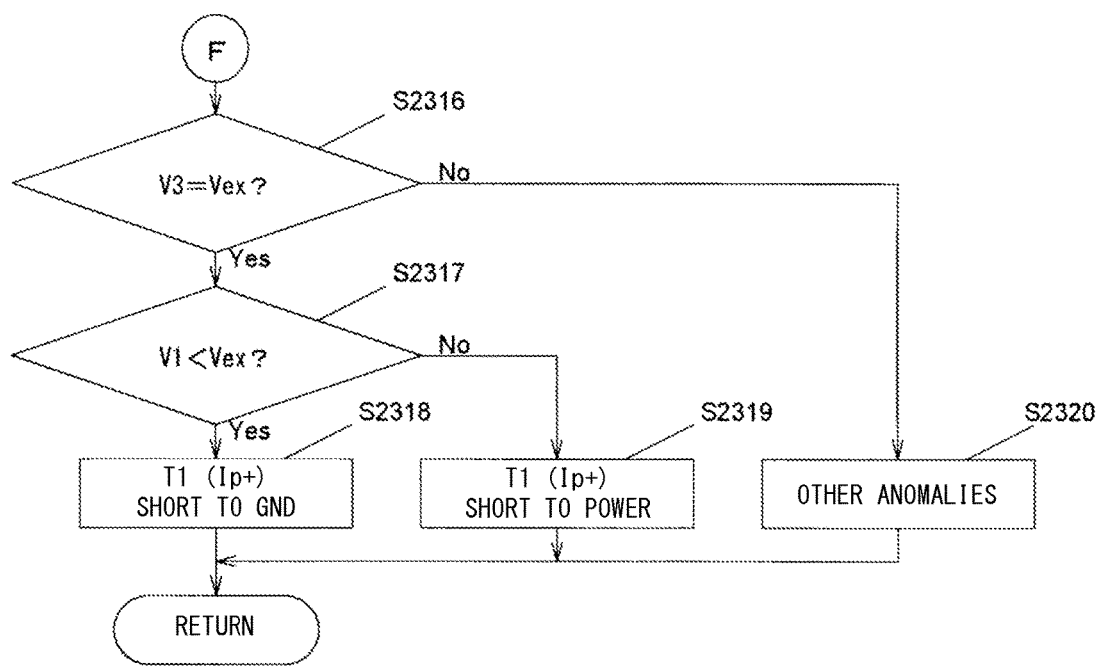
FIG. 12 is a third flowchart showing operation of the digital signal processor of the gas sensor system according to the embodiment for executing the post-cooling short state judgment routine.

By the post-cooling short state judgment routine shown in FIGS. 10 through 12, the processors 30 can judge, after the gas sensor 2 has cooled, six types of states in total, including three types of short-to-GND states (the first short-to-GND state, the second short-to-GND state, and the third short-to-GND state) and three types of short-to-power states (the first short-to-power state, the second short-to-power state, and the third short-to-power state), as well as other anomalies, based on the first terminal potential V1, the second terminal potential V2, and the third terminal potential V3 detected in step S22.

In the present embodiment, of the components of the sensor control section 40, the A/D converter 41 for detecting the first terminal potential V1 corresponds to the first terminal potential detection circuit. The A/D converter 42 for detecting the second terminal potential V2 corresponds to the second terminal potential detection circuit, and the A/D converter 43 for detecting the third terminal potential V3 corresponds to the third terminal potential detection circuit. The operational amplifier 44 corresponds to the examination potential circuit and the reference potential circuit, and the fourth switch SW4 corresponds to the first potential switch and the second potential switch. The current DAC 47 corresponds to the pump current output circuit, and the third switch SW3 corresponds to the second current switch. The current DAC 48 corresponds to the detection cell current output circuit, and the fifth switch SW5 corresponds to the first current switch.

In the present embodiment, the processor 30 which executes step S5, step S15, and step S22 corresponds to the terminal potential detection means.

The processor 30 which executes step S6 and step S16 corresponds to the short presence/absence judgment means.

The processor 30 which executes step S8 (pre-heating short state judgment routine: steps S801 through S818) and step S23 (post-cooling short state judgment routine: steps S2301 through S2320) corresponds to the short state judgment means.

The processor 30 which executes step S1 corresponds to the hot restart judgment means, and the processor 30 which executes steps S18 and S19 corresponds to the first waiting means and the second waiting means.

The processor 30 which executes step S7, step S17, and step S24 corresponds to the first cutoff means, the first cutoff maintaining means, the second cutoff maintaining means, and the fourth cutoff means, and the processor 30 which executes step S2 and step S12 corresponds to the second cutoff means and the third cutoff means.

As described above, in the gas sensor system 1 of the present embodiment, by turning on the first switch SW1 and the second switch SW2, the first terminal T1 and the second terminal T2 are connected via the first circuit 45 (the first resistor R1), and the second terminal T2 and the third terminal T3 are connected via the second circuit 46 (the second resistor R2). As a result, the first circuit 45 (the first resistor R1) is connected in parallel with the oxygen pump cell 14, and the second circuit 46 (the second resistor R2) is connected in parallel with the oxygen concentration detection cell 24. In this state, the examination potential Vex is applied to the second terminal T2.

As a result, irrespective of the temperature of the gas sensor 2; i.e., irrespective of whether the gas sensor 2 is in the high-temperature state (including the activated state) or in the low-temperature state (including the state in which the cells do not exhibit oxygen ion conductivity), the presence/absence of short anomaly of the gas sensor 2 can be judged based on the first terminal potential V1, the second terminal potential V2, and the third terminal potential V3 detected by the A/D converters 41, 42, and 43 (step S6 and step S16).

In the case where the gas sensor 2 is in the low-temperature state in which the temperature of the gas sensor 2 is lower than that in the activated state, by detecting the first terminal potential V1, the second terminal potential V2, and the third terminal potential V3 using the A/D converters 41, 42, and 43, the location where a short anomaly of the gas sensor 2 has occurred and the source (end) of the short-circuit (short to the ground potential GND or short to the power supply potential (the battery potential VB)) can be determined through diagnosis based on the detected first, second, and third terminal potentials V1, V2, and V3 (step S8 and step S23).

The gas sensor system 1 of the present embodiment includes the short presence/absence judgment means (step S6 and step S16). This short presence/absence judgment means (step S6 and step S16) judges the presence/absence of a short anomaly of the gas sensor 2. This is because the judgment of the presence/absence of a short anomaly of the gas sensor 2 can be performed irrespective of whether the gas sensor 2 is in the low-temperature state (step S6) or in the high-temperature state (step S16) as described above.

Namely, in this system 1, the judgment of the presence/absence of short anomaly of the gas sensor 2 can be performed not only when the internal resistances of the oxygen pump cell 14 and the oxygen concentration detection cell 24 are low (when the temperature of the gas sensor 2 is high) but also when the internal resistances of these cells are high (when the temperature of the gas sensor 2 is low).

Accordingly, in this system 1, irrespective of the temperature of the gas sensor 2, the presence/absence of short anomaly of the gas sensor 2 can be judged by the short presence/absence judgment means (step S6 and step S16).

In the gas sensor system 1 of the present embodiment, since the judgment as to whether or not all of the first terminal potential V1, the second terminal potential V2, and the third terminal potential V3 are equal to the examination potential Vex is made by the short presence/absence judgment means (step S6 and step S16), the presence/absence of a short anomaly of the gas sensor 2 can be judged properly. This is because, if no short has occurred, when the examination potential Vex is applied to the second terminal T2, all the first terminal potential V1, the second terminal potential V2, and the third terminal potential V3 become equal to the examination potential Vex due to the presence of the first resistor R1 and the second resistor R2.

The gas sensor system 1 of the present embodiment includes the short state judgment means (step S8 and step S23) for judging the short state, including the location where a short anomaly has occurred and the source (end) of the short-circuit, when the gas sensor 2 is in the low-temperature state. Therefore, it is possible to judge not only the presence/absence of a short anomaly but also the short state, which are then reported to the ECU 100 (step S9 and step S25).

In the gas sensor system 1 of the present embodiment, the short state judgment means (step S8 and step S23) judges six types of states in total, including three types of short-to-GND states and three types of short-to-power states, on the basis of the first terminal potential V1, the second terminal potential V2, and the third terminal potential V3. Therefore, when a short anomaly occurs, its short state can be judged properly.

In the gas sensor system 1 of the present embodiment, the short state judgment means (step S8 and step S23) distinguishes six types of states from one another based on the first terminal potential V1 through the third terminal potential V3. Therefore, the six types of short states can be judged properly.

In the gas sensor system 1 of the present embodiment, in the case where the startup is not a hot restart, the presence/absence of a short anomaly is judged in a state in which the gas sensor 2 is in the low-temperature state (step S6), and when the gas sensor 2 is judged to have a short anomaly, the location where the short anomaly has occurred and the source (end) of the short-circuit (short state) are determined immediately after the judgment (step S8). Meanwhile, in the case where the startup is a hot restart, the presence/absence of a short anomaly of the gas sensor 2 is judged in a state in which the gas sensor 2 is in the high-temperature state after the hot restart (step S16), and when the gas sensor 2 is judged to have a short anomaly, the location of the short anomaly and the source (end) of the short-circuit (short state) are determined (step S23) after waiting until the gas sensor 2 has assumed the low-temperature state (steps S18 and S19).

As a result, in the case where no short anomaly has occurred, the system can proceed to the step (wire breakage diagnosis) subsequent to the short anomaly diagnosis in the state in which the temperature of the gas sensor 2 is high. In addition, in the case of hot restart as well, the steps up to judgment of the short state can be performed properly.

In the gas sensor system 1 of the present embodiment, the presence/absence of a short anomaly is judged when a short anomaly diagnosis timing during operation of the gas sensor 2 is implemented; i.e., when the gas sensor 2 is activated (step S16). When the gas sensor 2 is judged to have a short anomaly, the location where the short anomaly has occurred and the source (end) of the short-circuit (short state) are judged (step S23) after waiting until the gas sensor 2 has assumed the low-temperature state (steps S18 and S19).

By virtue of this configuration, in the system 1, the short state can also be judged not only after startup of the system 1, but also in a period during which the gas sensor 2 is operating.

In the gas sensor system 1 of the present embodiment, in the case where the short presence/absence judgment means (step S6 and step S16) judges that a short anomaly is present, application of the examination potential Vex is discontinued (the fourth switch SW4 is turned off) by the step S7, step S17 and step S24 (the first cutoff means). As a result, when a short anomaly is present, application of the examination potential Vex to the second terminal T2 is discontinued.

In the gas sensor system 1 of the present embodiment, in the case where the short presence/absence judgment means (step S6 and step S16) judges that a short anomaly is present, the first switch SW1 and the second switch SW2 are also turned off, whereby the first circuit 45 and the second circuit 46 are disconnected. As a result, when the gas sensor 2 has a short anomaly, the connections between the terminals (the first terminal T1 through the third terminal T3) of the gas sensor 2 established by the first circuit 45 and the second circuit 46 are broken, whereby the states of the first terminal T1 through the third terminal T3 can be returned to their initial states before diagnosing the short anomaly.

In the gas sensor system 1 of the present embodiment, in the case where the gas sensor 2 is judged to have a short anomaly, the pump current Ip supplied to the oxygen pump cell 14 and the detection cell current (the minute current Icp, etc.) supplied to the oxygen concentration detection cell 24 are maintained in a cut-off state (step S7, step S17, and step S24). Therefore, it is possible to prevent blackening of the oxygen pump cell 14 and the oxygen concentration detection cell 24, which blackening would otherwise occur when the pump current Ip and/or the minute current Icp is supplied in the state in which a short anomaly were to continue.

In the gas sensor system 1 of the present embodiment, the operational amplifier 44, which serves as an examination potential circuit for applying the examination potential Vex, also serves as a reference potential circuit for applying the reference potential Vref after the gas sensor 2 is activated (the examination potential Vex=the reference potential Vref=+2.5 V). Therefore, it is unnecessary to provide a dedicated examination potential circuit for diagnosing a short anomaly.

In the gas sensor system 1 of the present embodiment, in the case where the gas sensor 2 is judged to have a short anomaly, application of the reference potential Vref (=the examination potential Vex) is discontinued (step S7, step S17, and step S24). Therefore, it is possible to prevent blackening of the oxygen pump cell 14 and the oxygen concentration detection cell 24, which blackening would otherwise occur when the reference potential Vref (=the examination potential Vex) is applied in the state in which a short anomaly continues.

The present invention has been described based on the above embodiment. However, needless to say, the present invention is not limited thereto and can be modified without departing from the scope of the invention.

For example, in the embodiment, the gas sensor 2 is an air-fuel-ratio sensor (full-range air-fuel-ratio sensor) which detects the concentration of oxygen (air-fuel ratio) within exhaust gas EG. However, the "gas sensor" is not limited to the air-fuel-ratio sensor, and may be an NOx sensor for detecting the concentration of nitrogen oxide (NOx).

Also, the sensor control section 40 may be incorporated into the ECU 100.

In the gas sensor system 1 of the embodiment, the sensor control section 40 is constituted by an ASIC including the digital signal processor 30, and the PID control of the pump current Ip is performed by a digital scheme.

However, the present invention can be applied to a gas sensor system which has a sensor control section composed of an ASIC including an analog PID circuit and a separately provided microprocessor and in which the PID control is performed by an analog scheme.

In the embodiment, the first waiting means and the second waiting means for waiting until the gas sensor 2 has assumed the low-temperature state discontinue supply of electric current to the heater section 80 and wait until a predetermined cooling wait time (for example, 60 seconds) elapses (steps S18 and S19). However, the embodiment may be modified to judge whether the temperature of the gas sensor 2 is high or low or whether the gas sensor 2 has actually reached the low-temperature state by, for example, detecting the temperature of the gas sensor 2 using a temperature sensor.

The invention has been described in detail with reference to the above embodiments. However, the invention should not be construed as being limited thereto. It should further be apparent to those skilled in the art that various changes in form and detail of the invention as shown and described above may be made. It is intended that such changes be included within the spirit and scope of the claims appended hereto.

This application is based on Japanese Patent Application No. 2014-203299 filed Oct. 1, 2014, incorporated herein by reference in its entirety.

What is claimed is:

1. A gas sensor system comprising:
   a gas sensor having an oxygen pump cell electrically communicating with a first terminal and a second terminal, and an oxygen concentration detection cell communicating with the second terminal and a third terminal, wherein the gas sensor has an activated state in which both the oxygen pump cell and the oxygen concentration detection cell exhibit oxygen ion conductivity and an inactivated state in which at least one of the oxygen pump cell or the oxygen concentration detection cell does not exhibit oxygen ion conductivity; and
   a sensor control section which includes a first terminal potential detection circuit for detecting a first terminal potential of the first terminal, a second terminal potential detection circuit for detecting a second terminal potential of the second terminal, and a third terminal potential detection circuit for detecting a third terminal potential of the third terminal and which controls the gas sensor through the first terminal, the second terminal, and the third terminal, wherein
   the sensor control section includes:
   an examination potential circuit for applying to the second terminal a predetermined examination potential which is higher than a ground potential and is lower than a power supply potential of a power supply for control of the sensor control section;
   a first circuit for disconnectably connecting the first terminal and the second terminal, the first circuit having a resistance which is lower than an input resistance of the first terminal potential detection circuit, is lower than an internal resistance of the oxygen pump cell when the gas sensor is in the inactivated state, and is higher than the internal resistance of the oxygen pump cell when the gas sensor is in the activated state;
   a second circuit for disconnectably connecting the second terminal and the third terminal, the second circuit having a resistance which is lower than an input resistance of the third terminal potential detection circuit, is lower than an internal resistance of the oxygen concentration detection cell when the gas sensor is in the inactivated state, and is higher than the internal resistance of the oxygen concentration detection cell when the gas sensor is in the activated state; and
   terminal potential detection means for detecting the first terminal potential, the second terminal potential, and the third terminal potential using the first terminal potential detection circuit, the second terminal potential detection circuit, and the third terminal potential detection circuit when the examination potential is applied to the second terminal and the first circuit and the second circuit are connected.

2. The gas sensor system as claimed in claim 1, wherein the sensor control section includes short presence/absence judgment means for judging whether or not a short anomaly of the gas sensor is present based on the first terminal potential, the second terminal potential, and the third terminal potential detected by the terminal potential detection means.

3. The gas sensor system as claimed in claim 2, wherein the short presence/absence judgment means judges whether or not all of the detected first terminal potential, the detected second terminal potential, and the detected third terminal potential are equal to the examination potential.

4. The gas sensor system as claimed in claim 2, wherein the sensor control section includes short state judgment means, operable when the short presence/absence judgment means judges that a short anomaly is present, for judging a short state, including a location where the short anomaly of the gas sensor has occurred and a source of the short-circuit, based on the first terminal potential, the second terminal potential, and the third terminal potential detected by the terminal potential detection means, when the gas sensor is in the inactivated state.

5. The gas sensor system as claimed in claim 4, wherein the short state judgment means judges, based on the detected first terminal potential, the detected second terminal potential, and the detected third terminal potential, six types of short states,
   the six types of short states including:
   a first short-to-GND state in which a first wiring line for connecting the oxygen pump cell to the first terminal is shorted to the ground potential,
   a second short-to-GND state in which a second wiring line for connecting the oxygen pump cell and the oxygen concentration detection cell to the second terminal is shorted to the ground potential,
   a third short-to-GND state in which a third wiring line for connecting the oxygen concentration detection cell to the third terminal is shorted to the ground potential,
   a first short-to-power state in which the first wiring line is shorted to a power supply potential,
   a second short-to-power state in which the second wiring line is shorted to the power supply potential, and
   a third short-to-power state in which the third wiring line is shorted to the power supply potential.

6. The gas sensor system as claimed in claim 5, wherein the short state judgment means judges, based on the detected first terminal potential, the detected second terminal potential, and the detected third terminal potential,
   that the gas sensor is in the first short-to-GND state when the second terminal potential and the third terminal potential are equal to the examination potential and the first terminal potential is lower than the examination potential,
   that the gas sensor is in the second short-to-GND state when all of the first terminal potential, the second terminal potential, and the third terminal potential are lower than the examination potential,
   that the gas sensor is in the third short-to-GND state when the first terminal potential and the second terminal potential are equal to the examination potential and the third terminal potential is lower than the examination potential, that the gas sensor is in the first short-to-power state when the second terminal potential and the third terminal potential are equal to the examination potential and the first terminal potential is higher than the examination potential, that the gas sensor is in the second short-to-power state when all of the first terminal potential, the second terminal potential, and the third terminal potential are higher than the examination potential, and that the gas sensor is in the third short-to-power state when the first terminal potential and the second terminal potential are equal to the examination potential and the third terminal potential is higher than the examination potential.

7. The gas sensor system as claimed in claim 4, wherein the sensor control section includes:
   hot restart judgment means for judging immediately after startup of the system whether or not the startup of the system is a hot restart; and
   first waiting means for waiting until the gas sensor assumes the low-temperature state, prior to judgment by the short state judgment means, when the hot restart judgment means judges that the startup is the hot restart and the short presence/absence judgment means judges that a short anomaly is present.

8. The gas sensor system as claimed in claim 4, wherein the sensor control section includes second waiting means for waiting until the gas sensor assumes the low-temperature state, prior to judgment by the short state judgment means, when the short presence/absence judgment means judges that a short anomaly is present while the gas sensor is operating in the activated state.

9. The gas sensor system as claimed in claim 4, wherein the sensor control section includes:
   a first potential switch for applying the examination potential of the examination potential circuit to the second terminal; and
   first cutoff means for turning off the first potential switch when the short presence/absence judgment means judges that a short anomaly is present.

10. The gas sensor system as claimed in claim 9, wherein the first cutoff means turns off the first potential switch, and disconnects the first circuit and the second circuit.

11. The gas sensor system as claimed in claim 4, wherein the gas sensor internally has a measurement chamber into which a gas under measurement is introduced and a reference oxygen chamber in which a reference oxygen atmosphere is generated;
   the oxygen concentration detection cell has a first detection electrode which faces the reference oxygen chamber and electrically communicates with the third terminal and a second detection electrode exposed to the measurement chamber and electrically communicates with the second terminal; and
   the sensor control section includes:
   a detection cell current output circuit for supplying a detection cell current to the oxygen concentration detection cell through the third terminal,
   a first current switch for turning on and turning off supply of the detection cell current from the detection cell current output circuit to the oxygen concentration detection cell through the third terminal,
   second cutoff means for turning off the first current switch in a period during which the short presence/absence judgment means judges whether or not a short anomaly is present, and
   first cutoff maintaining means for maintaining the first current switch in an off state when the short presence/absence judgment means judges that a short anomaly is present.

12. The gas sensor system as claimed in claim 4, wherein the gas sensor internally has a measurement chamber into which a gas under measurement is introduced;
   the oxygen pump cell has a first pump electrode disposed outside the measurement chamber which electrically communicates with the first terminal and a second pump electrode exposed to the measurement chamber which electrically communicates with the second terminal; and
   the sensor control section includes:
   a pump current output circuit for supplying a pump current to the oxygen pump cell through the first terminal,
   a second current switch for turning on and turning off supply of the pump current from the pump current output circuit to the oxygen pump cell through the first terminal,
   third cutoff means for turning off the second current switch in a period during which the short presence/absence judgment means judges whether or not a short anomaly is present, and
   second cutoff maintaining means for maintaining the second current switch in an off state when the short presence/absence judgment means judges that a short anomaly is present.

13. The gas sensor system as claimed in claim 4, wherein the examination potential circuit also functions as a reference potential circuit which applies a reference potential to the second terminal after the gas sensor is activated.

14. The gas sensor system as claimed in claim 13, wherein the sensor control section includes:
   a second potential switch for turning on and turning off application of the examination potential and the reference potential from the reference potential circuit to the second terminal, and
   fourth cutoff means for turning off the second potential switch when the short presence/absence judgment means judges that a short anomaly is present.

15. The gas sensor system as claimed in claim 1, wherein the first circuit includes a switch and one or more resistors connected in parallel with the oxygen pump cell, and the second circuit includes a switch and one or more resistors connected in parallel with the oxygen concentration detection cell.

* * * * *